(12) United States Patent
Chung et al.

(10) Patent No.: US 9,431,616 B2
(45) Date of Patent: Aug. 30, 2016

(54) PHOSPHAPHENANTHRENE-CARBAZOLE-BASED ORGANIC LIGHT-EMITTING COMPOUND, AND ORGANIC LIGHT-EMITTING DEVICE COMPRISING SAME

(75) Inventors: Kwang Choon Chung, Yongin-si (KR); Hyun Nam Cho, Gunpo-si (KR); Ji Hoon Yoo, Bucheon-si (KR); Yun Ho Jung, Ansan-si (KR)

(73) Assignee: INKTEC CO., LTD., Ansan-Si, Gyunggi-Do (KR)

( * ) Notice: Subject to any disclaimer, the term of this patent is extended or adjusted under 35 U.S.C. 154(b) by 677 days.

(21) Appl. No.: 13/813,296

(22) PCT Filed: Jul. 29, 2011

(86) PCT No.: PCT/KR2011/005604
§ 371 (c)(1),
(2), (4) Date: Mar. 15, 2013

(87) PCT Pub. No.: WO2012/015269
PCT Pub. Date: Feb. 2, 2012

(65) Prior Publication Data
US 2013/0161603 A1    Jun. 27, 2013

(30) Foreign Application Priority Data

Jul. 30, 2010   (KR) .......................... 10-2010-0073957
Nov. 2, 2010    (KR) .......................... 10-2010-0108438

(51) Int. Cl.
| | | |
|---|---|---|
| H01L 51/00 | (2006.01) | |
| C07F 9/6571 | (2006.01) | |
| C07F 9/6581 | (2006.01) | |
| C09K 11/06 | (2006.01) | |
| H05B 33/14 | (2006.01) | |
| H01L 51/50 | (2006.01) | |

(52) U.S. Cl.
CPC ....... *H01L 51/0072* (2013.01); *C07F 9/65719* (2013.01); *C07F 9/657172* (2013.01); *C09K 11/06* (2013.01); *H05B 33/14* (2013.01); *C09K 2211/1096* (2013.01); *H01L 51/0085* (2013.01); *H01L 51/5016* (2013.01)

(58) Field of Classification Search
CPC .................... C07F 9/657172; C07F 9/65719; C09K 11/06; C09K 2211/1096; H01L 51/0072; H01L 51/0085; H01L 51/5016; H05B 33/14
See application file for complete search history.

(56) References Cited

U.S. PATENT DOCUMENTS

2002/0193522 A1   12/2002   Sun
2010/0252818 A1   10/2010   Chung et al.

FOREIGN PATENT DOCUMENTS

| JP | 2002-193985 | 7/2002 |
|---|---|---|
| JP | 2006-328100 | * 12/2006 |
| JP | 2007-091606 | * 4/2007 |
| KR | 10-2008-0091036 | 10/2008 |

OTHER PUBLICATIONS

Sun, Y.-M. et al., "Synthesis and luminescent characteristics of novel phosphorus containing light-emitting polymers", Polymer, Oct. 9, 2000, vol. 42, No. 3, pp. 1035-1045. ISSN: 0032-3861.

* cited by examiner

*Primary Examiner* — Dawn Garrett
(74) *Attorney, Agent, or Firm* — Hauptman Ham, LLP

(57) ABSTRACT

Provided are a phosphaphenanthrene-carbazole-based organic light-emitting compound having superior light emitting properties, and an organic light-emitting device including the same.

12 Claims, 3 Drawing Sheets

PHOSPHAPHENANTHRENE-CARBAZOLE-BASED ORGANIC LIGHT-EMITTING COMPOUND, AND ORGANIC LIGHT-EMITTING DEVICE COMPRISING SAME

TECHNICAL FIELD

The present invention relates to a phosphaphenanthrene-carbazole-based organic light-emitting compound having superior light-emitting properties, and an organic light-emitting device including the same.

BACKGROUND ART

A organic light-emitting device, which is a self light-emitting device, has various advantages such as a wide viewing angle, a rapid response speed, a low driving voltage, or the like, and is currently applied as a next generation flat panel display.

Generally, a basic configuration of the organic light-emitting device has a multilayer thin film structure in which a hole transport layer, a light-emitting layer, and electron transport layer that are made of organic compounds are multilayered between an anode and a cathode. The organic light-emitting device uses a principle that when electricity is applied between both electrodes, electrons are injected from the cathode and holes are injected from the anode, such that the electrons are re-combined with holes in the light emitting layer and light is emitted while an excited state energy level is decreased to a ground state energy level.

Since Eastman Kodak Corp. (US) announced that they developed a device using aromatic diamine and Alq3 as a material for forming a light-emitting layer in 1987 (Appl. Phys. Lett. p913, (1987)), research into a technology of improving performance of a phosphorescent light-emitting material such as a naphthyldiamine based light-emitting material (U.S. Pat. No. 6,549,345), a fluorescent light-emitting material such as anthracene based material (U.S. Pat. No. 6,803,121), and a light-emitting material using an iridium complex having higher efficiency ((U.S. Pat. No. 6,858,327) has been conducted. Actually, this phosphorescent light emitting material is currently applied to a small size flat panel display such as a mobile phone, or the like.

Meanwhile, in order to maximize energy transfer efficiency, a host material is generally used in the phosphorescent light emitting material. For example, as a low molecular weight phosphorescent host, there are 4,4-N,N-dicarbazole-biphenyl (CBP) and 1,3-bis(9-carbazolyl)benzene (mCP), and the like (Journal of Materials Chemistry (2003) 13, 2157-2163; Journal of Materials Chemistry (2005) 15, 2304-2315), and as a high molecular weight phosphorescent host, there are poly(N-vinylcarbazole)(PVK), and the like.

Recently, an organic light-emitting device having a monolayer structure and a multi-layer structure using polyvinylcarbazole, which is a polymer, rather than CBF or mCP as the host in the phosphorescent device is reported by C.W. Tang Group (J. Appl. Phys., Vol. 92, No. 7, 3447).

However, in the light-emitting device, disadvantages such as degradation of the device by heat generated by the driving for a long time, or the like, may be generated. Particularly, since a material such as mCP has a low glass transition temperature Tg, in the case in which a device made using this material as a material for a thin film is driven, the device may be easily crystallized, such that color purity may be changed by heat and a life span of the device may be decreased.

Therefore, in developing a material for organic light emitting diode (OLED) device having a long life span and high efficiency, band-gap energy of the host material and heat resistance of the material that determine the color purity and efficiency are important variables. Particularly, in developing a blue phosphorescent host material, effects of the band-gap energy of the host material and heat resistance of the material are significantly large. Researches into a technology of improving efficiency and color purity through substitution at 3 and 6 positions of the carbazole have been conducted, but the expected effect or more was not shown.

The present inventors have continuously studied in order to solve this problem and thus developed a host material capable of implementing excellent color purity and high efficiency by introducing a phosphorus compound at 3 or 6 positions of carbazole compounds to increase band-gap energy between a highest unoccupied molecular orbital (HOMO) energy level and a lowest unoccupied molecular orbital (LUMO) energy level of the host material.

Particularly, a novel host material having wide band-gap energy as well as heat resistance was obtained by synthesizing a host material in which phosphaphenanthrene based derivatives that is a phosphorus compound and has excellent heat resistance and carbazole based derivatives are bonded with each other, and a configuration of the organic light-emitting device was successfully progressed.

DISCLOSURE

Technical Problem

An object of the present invention is to provide a phosphaphenanthrene-carbazole-based organic light-emitting compound having superior wide band gap energy, heat resistance, and light-emitting properties that are required to implement a device having high efficiency and a long life span, and an organic light-emitting device including the same.

Technical Solution

In one general aspect, a phosphaphenanthrene-carbazole-based organic light-emitting compound may have superior heat resistance and light-emitting properties to thereby be used as a core material for an organic light emitting diode (OLED) and be represented by the following Chemical Formula 1.

[Chemical Formula 1]

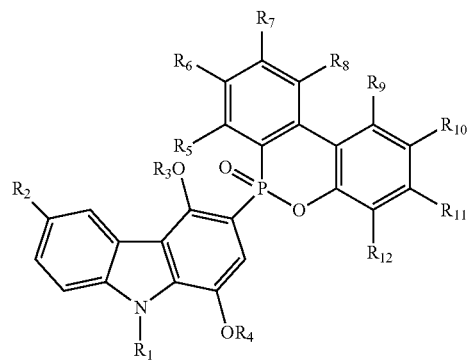

[In Chemical Formula 1, $R_1$ may be hydrogen, $(C_1\text{-}C_{30})$alkyl, $(C_6\text{-}C_{30})$aryl, $(C_3\text{-}C_{30})$ heteroaryl, $(C_2\text{-}C_{10})$alkenyl, $(C_2\text{-}C_{18})$alkynyl, amino, mono- or di-$(C_1\text{-}C_{30})$alkylamino, or mono- or di-$(C_6\text{-}C_{30})$arylamino;

$R_2$ may be hydrogen, hydroxy, $(C_1\text{-}C_{30})$alkyl, $(C_6\text{-}C_{30})$ aryl, $(C_3\text{-}C_{30})$ heteroaryl, N-carbazolyl, $(C_2\text{-}C_{10})$alkenyl, $(C_2\text{-}C_{18})$alkynyl, $(C_6\text{-}C_{30})$ aryloxy, $(C_1\text{-}C_{18})$alkyloxy, $(C_1\text{-}C_{30})$alkylcarbonyloxy, amino, mono- or di-$(C_1\text{-}C_{30})$alkylamino, or mono- or di-$(C_6\text{-}C_{30})$arylamino;

$R_3$ and $R_4$ each may be independently hydrogen, $(C_1\text{-}C_{30})$alkyl, $(C_6\text{-}C_{30})$ aryl, $(C_3\text{-}C_{30})$ heteroaryl, $(C_6\text{-}C_{30})$ar$(C_1\text{-}C_{30})$alkyl, $(C_2\text{-}C_{10})$alkenyl, $(C_2\text{-}C_{18})$alkynyl$(C_1\text{-}C_{30})$alkylcarbonyl, $(C_2\text{-}C_{10})$alkenylcarbonyl, amino, mono- or di-$(C_1\text{-}C_{30})$alkylamino, or mono- or di-$(C_6\text{-}C_{30})$ arylamino;

$R_5$ to $R_{12}$ may be the same as or different from each other, each independently, and independently hydrogen, straight- or branched-chain $(C_1\text{-}C_{30})$alkyl, straight- or branched-chain $(C_1\text{-}C_{30})$alkyl containing oxygen, nitrogen or sulfur, $(C_1\text{-}C_{30})$alkoxy, $(C_3\text{-}C_{30})$cycloalkyl, $(C_3\text{-}C_{30})$cycloalkyl$(C_1\text{-}C_{30})$alkyl, $(C_6\text{-}C_{30})$ aryl, halogen, cyano, amino, mono- or di-$(C_1\text{-}C_{30})$alkylamino, mono- or di-$(C_6\text{-}C_{30})$arylamino, hydroxy, nitro, mono- or di-benzylamino, or $(C_3\text{-}C_{30})$cycloalkylamino, $R_5$ to $R_{12}$ may be bonded to carbon of substituent adjacent thereto via $(C_3\text{-}C_5)$alkylene or $(C_3\text{-}C_5)$ alkenyl to form a fused ring, and a carbon in the fused ring may be substituted with a hetero atom selected from oxygen, sulfur, or nitrogen;

aryl, heteroaryl, alkenyl, alkynyl, or amino of $R_1$, aryl, heteroaryl, N-carbazolyl, alkenyl, alkynyl, aryloxy, alkyloxy, or amino of $R_2$, and alkyl, aryl, heteroaryl, aralkyl, alkenyl, alkynyl, or amino of $R_3$ and $R_4$ may be further substituted with at least one selected from straight- or branched-chain $(C_1\text{-}C_{30})$alkyl substituted or unsubstituted with halogen, $(C_3\text{-}C_{30})$cycloalkyl, $(C_3\text{-}C_{30})$cycloalkyl$(C_1\text{-}C_{30})$alkyl, $(C_2\text{-}C_{10})$alkenyl, $(C_2\text{-}C_{10})$alkynyl, $(C_6\text{-}C_{30})$ aryl, straight- or branched chain $(C_1\text{-}C_{30})$alkyl containing oxygen, nitrogen or sulfur, $(C_1\text{-}C_{30})$alkoxy, $(C_3\text{-}C_{30})$ heteroaryl, N-carbazolyl, 3- to 7-membered heterocycloalkyl containing at least one of oxygen, nitrogen or sulfur in the hetero ring, cyano, halogen, 9-oxa-10-phosphaphenathrene-10-oxide, $(C_6\text{-}C_{30})$ aryloxy, $(C_6\text{-}C_{30})$ arylsulfonyl, amino, mono- or di-$(C_1\text{-}C_{30})$alkylamino, mono- or di-$(C_6\text{-}C_{30})$arylamino, mono- or di-benzylamino, mono- or di-$(C_3\text{-}C_{30})$cycloalkylamino, hydroxyl, nitro, $(C_2\text{-}C_7)$alkenyloxy, $(C_2\text{-}C_7)$alkynyloxy, $(C_2\text{-}C_7)$alkenylcarbonyloxy, $(C_2\text{-}C_7)$alkynylcarbonyloxy, tri$(C_1\text{-}C_{30})$alkylsilyl, di$(C_1\text{-}C_{30})$alkyl$(C_6\text{-}C_{30})$ arylsilyl, di$(C_6\text{-}C_{30})$ ar $(C_1\text{-}C_{30})$alkylsilyl, and tri$(C6\text{-}C30)$ arylsilyl, and alkyl, alkenyl, alkynyl, aryl, alkoxy, heteroaryl, N-carbazolyl, 9-oxa-10-phosphaphenathrene-10-oxide, aryloxy, arylsulfonyl, alkenyloxy, alkynyloxy, alkenylcarbonyloxy, alkynylcarbonyloxy, trialkylsilyl, dialkylarylsilyl, diarylalkylsilyl, and triarylsilyl substituted with aryl, heteroaryl, alkenyl, alkynyl, or amino of $R_1$, aryl, heteroaryl, N-carbazolyl, alkenyl, alkynyl, aryloxy, alkyloxy, or amino of $R_2$, and alkyl, aryl, heteroaryl, aralkyl, alkenyl, alkynyl or amino of $R_3$ and $R_4$ may be further substituted with at least one selected from straight- or branched-chain $(C_1\text{-}C_{30})$alkyl substituted or unsubstituted with halogen, $(C_2\text{-}C_{10})$alkenyl substituted or unsubstituted with halogen, $(C_2\text{-}C_{10})$alkynyl substituted or unsubstituted with halogen, $(C_6\text{-}C_{30})$ aryl, amino, 3- to 7-membered heterocycloalkyl containing at least one of oxygen, nitrogen or sulfur in the hetero ring, $(C_1\text{-}C_7)$alkylcarbonyl, $(C_2\text{-}C_7)$alkenylcarbonyl, $(C_2\text{-}C_7)$alkynylcarbonyl, $(C_1\text{-}C_7)$alkyl$(C_2\text{-}C_7)$alkenylcarbonyl, or $(C_1\text{-}C_7)$alkyl $(C_2\text{-}C_7)$alkynylcarbonyl.]

In Chemical Formula 1, preferably, $R_1$ may be $(C_1\text{-}C_{30})$ alkyl, $(C_6\text{-}C_{30})$ aryl, $(C_3\text{-}C_{30})$ heteroaryl, $(C_2\text{-}C_{10})$alkenyl, or $(C_2\text{-}C_{10})$alkynyl; and alkyl, aryl, heteroaryl, alkenyl, and alkynyl of $R_1$ may be further substituted with at least one selected from straight- or branched-chain $(C_1\text{-}C_{30})$alkyl substituted or unsubstituted with halogen, $(C_2\text{-}C_{10})$alkenyl, $(C_2\text{-}C_{10})$alkynyl, $(C_6\text{-}C_{30})$ aryl, straight- or branched-chain $(C_1\text{-}C_{30})$alkyl containing oxygen, nitrogen, or sulfur, $(C_1\text{-}C_{30})$ alkoxy, $(C_3\text{-}C_{30})$ heteroaryl, cyano, halogen, $(C_6\text{-}C_{30})$ aryloxy, $(C_6\text{-}C_{30})$ arylsulfonyl, mono- or di-$(C_1\text{-}C_{30})$alkylamino, mono- or di-$(C_6\text{-}C_{30})$ arylamino, $(C_2\text{-}C_{10})$alkenyloxy, $(C_2\text{-}C_{10})$alkynyloxy, $(C_2\text{-}C_{10})$alkenylcarbonyloxy, $(C_2\text{-}C_{10})$alkynylcarbonyloxy, tri$(C_2\text{-}C_{30})$alkylsilyl, di$(C_1\text{-}C_{30})$alkyl$(C_6\text{-}C_{30})$ arylsilyl, di$(C_6\text{-}C_{30})$ aryl$(C_1\text{-}C_{30})$alkylsilyl, and tri$(C_6\text{-}C_{30})$ arylsilyl, $R_2$ is hydrogen, $(C_1\text{-}C_{30})$alkyl, $(C_6\text{-}C_{30})$ aryl, N-carbazolyl, $(C_3\text{-}C_{30})$ heteroaryl, $(C_2\text{-}C_{10})$alkenyl, $(C_2\text{-}C_{10})$alkynyl, $(C_6\text{-}C_{30})$ aryloxy, $(C_1\text{-}C_{30})$alkyloxy, amino, mono- or di-$(C_1\text{-}C_{30})$alkylamino, or mono- or di-$(C_6\text{-}C_{30})$ arylamino, alkyl, aryl, N-carbazolyl, heteroaryl, alkenyl, alkynyl, aryloxy, alkyloxy, or amino of $R_2$ may be further substituted with $(C_1\text{-}C_{30})$alkyl substituted or unsubstituted with halogen, $(C_2\text{-}C_{10})$alkenyl, $(C_2\text{-}C_{10})$alkynyl, $(C_6\text{-}C_{30})$aryl, $(C_1\text{-}C_{30})$alkyl containing oxygen, nitrogen, or sulfur, $(C_1\text{-}C_{30})$ alkoxy, $(C_3\text{-}C_{30})$ heteroaryl, cyano, halogen, $(C_6\text{-}C_{30})$ aryloxy, $(C_6\text{-}C_{30})$ arylsulfonyl, mono- or di-$(C_1\text{-}C_{30})$alkylamino, mono- or di-$(C_6\text{-}C_{30})$ arylamino, $(C_2\text{-}C_{10})$alkenyloxy, $(C_2\text{-}C_{10})$alkynyloxy, $(C_2\text{-}C_{10})$alkenylcarbonyloxy, $(C_2\text{-}C_{10})$alkynylcarbonyloxy, tri$(C_1\text{-}C_{30})$alkylsilyl, di$(C_1\text{-}C_{30})$alkyl$(C_6\text{-}C_{30})$ arylsilyl, di$(C_6\text{-}C_{30})$aryl$(C_1\text{-}C_{30})$alkylsilyl, and tri$(C_6\text{-}C_{30})$ arylsilyl, each may be independently $(C_1\text{-}C_{30})$alkyl, $(C_6\text{-}C_{30})$ ar $(C_1\text{-}C_{30})$alkyl, or $(C_1\text{-}C_{30})$alkylcarbonyl, alkyl, aralkyl, and alkylcarbonyl of $R_3$ and $R_4$ may be further substituted with at least one selected from $(C_1\text{-}C_{30})$alkyl substituted or unsubstituted with halogen, $(C_2\text{-}C_{10})$alkenyl, $(C_2\text{-}C_{10})$alkynyl, $(C_6\text{-}C_{30})$ aryl, $(C_1\text{-}C_{30})$alkyl containing oxygen, nitrogen or sulfur, $(C_1\text{-}C_{30})$alkoxy, $(C_3\text{-}C_{30})$ heteroaryl, cyano, halogen, $(C_6\text{-}C_{30})$ aryloxy, $(C_6\text{-}C_{30})$ arylsulfonyl, mono- or di-$(C_1\text{-}C_{30})$alkylamino, mono- or di-$(C_6\text{-}C_{30})$ arylamino, $(C_2\text{-}C_{10})$alkenyloxy, $(C_2\text{-}C_{10})$alkynyloxy, $(C_2\text{-}C_{10})$alkenylcarbonyloxy, $(C_2\text{-}C_{10})$alkynylcarbonyloxy, tri$(C_1\text{-}C_{30})$alkylsilyl, di$(C_1\text{-}C_{30})$alkyl$(C_6\text{-}C_{30})$ arylsilyl, di$(C_6\text{-}C_{30})$ aryl$(C_1\text{-}C_{30})$alkylsilyl, and tri$(C_6\text{-}C_{30})$ arylsilyl, $R_5$ to $R_{12}$ may be the same as or different from each other and be independently hydrogen, $(C_1\text{-}C_{30})$alkyl, $(C_1\text{-}C_{30})$ alkyl containing oxygen, nitrogen or sulfur, $(C_1\text{-}C_{30})$alkoxy, $(C_3\text{-}C_{30})$cycloalkyl, $(C_3\text{-}C_{30})$cycloalkyl$(C_1\text{-}C_{30})$alkyl, $(C_6\text{-}C_{30})$aryl, halogen, cyano, amino, mono- or di-$(C_1\text{-}C_{30})$alkylamino, mono- or di-$(C_6\text{-}C_{30})$ arylamino, hydroxy, nitro, mono- or di-benzylamino, or $(C_3\text{-}C_{30})$cycloalkylamino, and $R_5$ and $R_{12}$ may be linked to carbon of substituent adjacent thereto via $(C_3\text{-}C_5)$alkylene or $(C_3\text{-}C_5)$alkenylene to form a fused ring, and carbon of the fused ring may be substituted with a hetero atom selected from oxygen, sulfur, and nitrogen.

More preferably, $R_1$ is $(C_1\text{-}C_{30})$alkyl or $(C_6\text{-}C_{30})$aryl, and aryl of $R_1$ may be further substituted with $(C_1\text{-}C_{30})$alkyl substituted or unsubstituted with halogen; $R_2$ is hydrogen, $(C_6\text{-}C_{30})$ aryl, or $(C_1\text{-}C_{30})$alkylcarbonyloxy, and aryl of $R_2$ may be further substituted with $(C_1\text{-}C_{30})$alkyl substituted or unsubstituted with halogen; $R_3$ and $R_4$ each may be independently $(C_1\text{-}C_{30})$alkyl, $(C_6\text{-}C_{30})$ ar $(C_1\text{-}C_{30})$alkyl, or $(C_1\text{-}C_{30})$alkylcarbonyl, and aralkyl of $R_3$ and $R_4$ may be further substituted with $(C_1\text{-}C_{30})$alkyl substituted or unsubstituted with halogen; and $R_5$ to $R_{12}$ may be the same as or different from each other and may be independently hydrogen.

The compound represented by Chemical Formula 1 may be, for example, compounds having the following structures, but the present invention is not limited thereto.
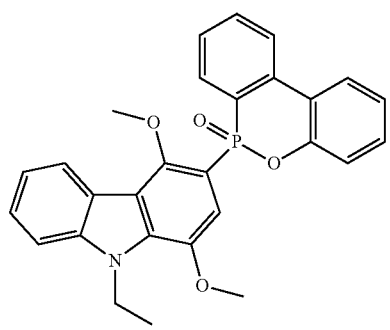
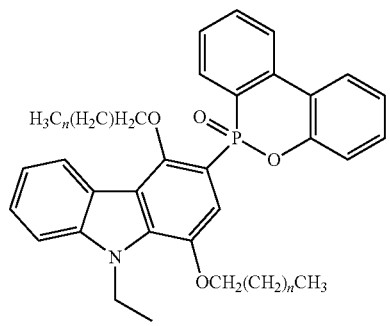
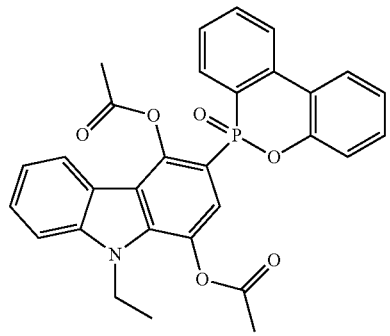
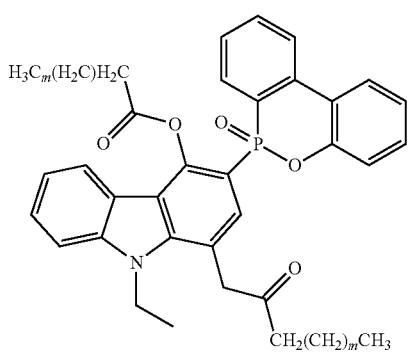
-continued
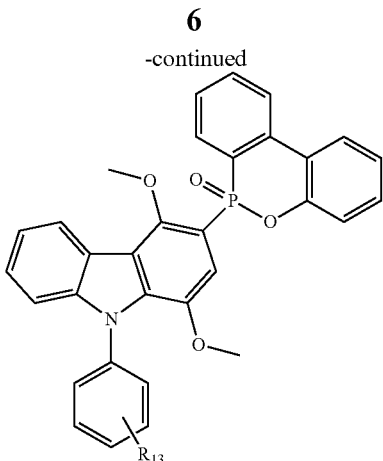
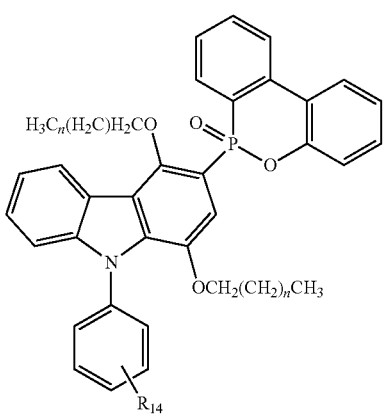
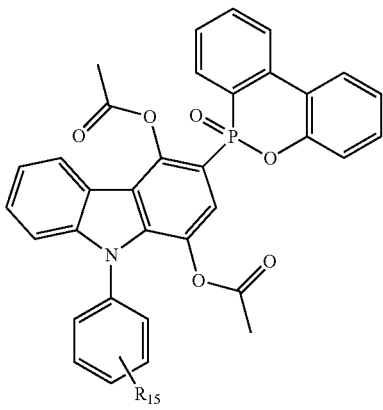
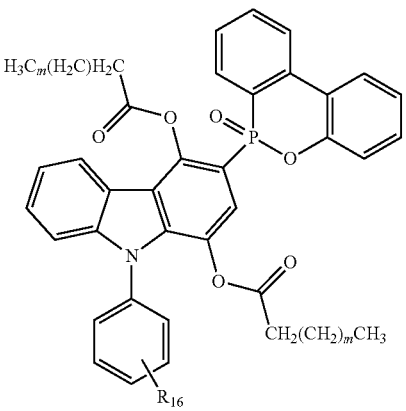

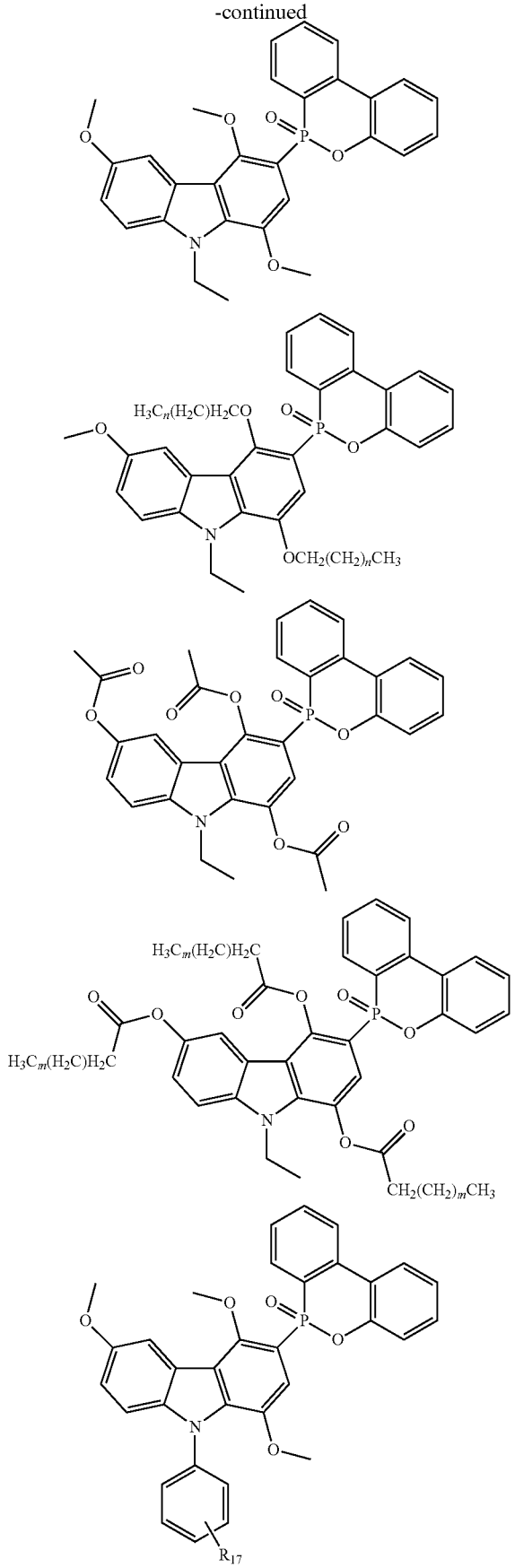

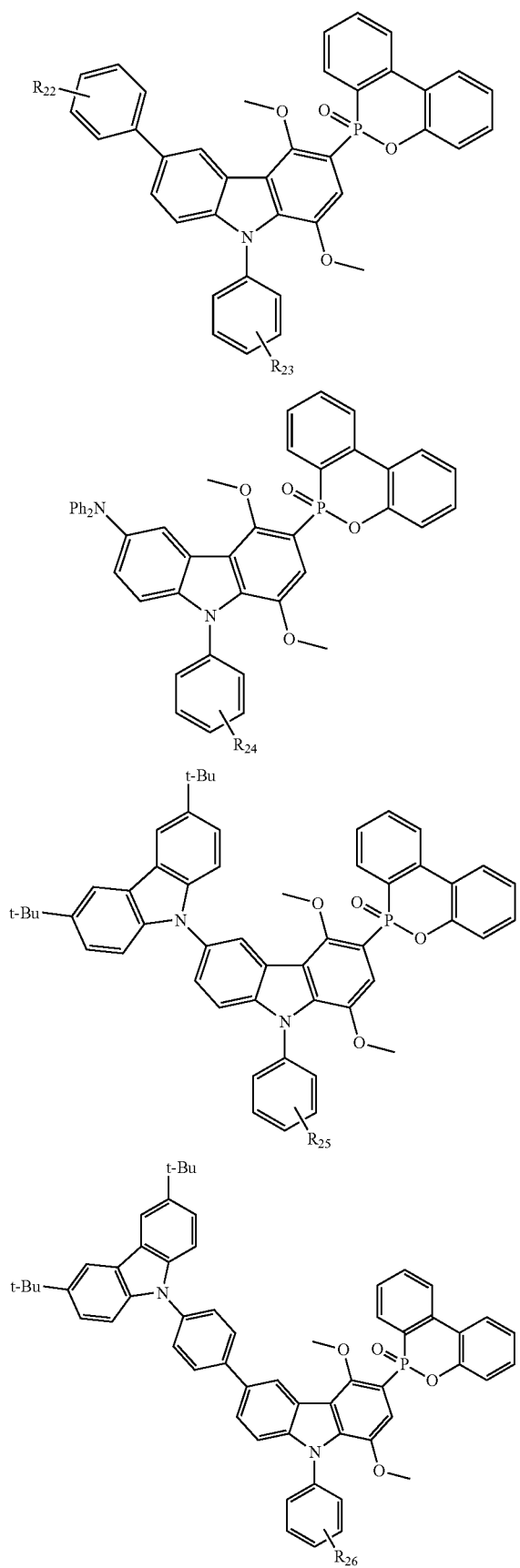
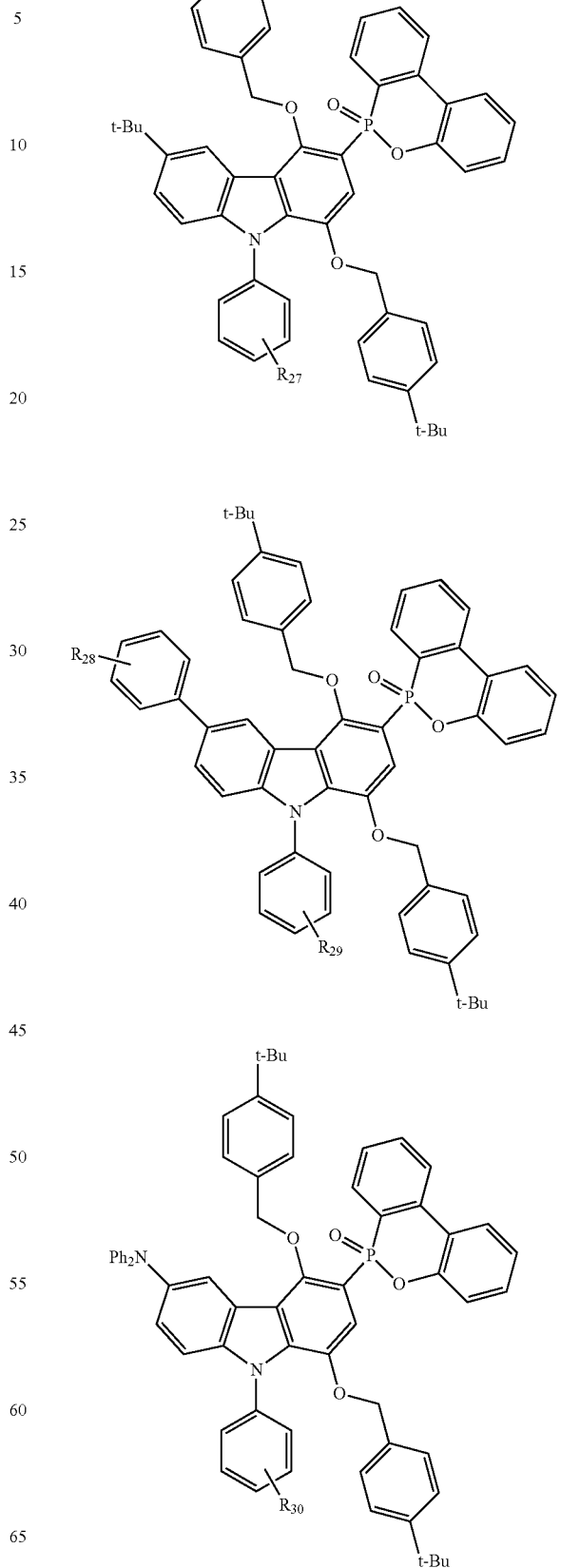

11
-continued
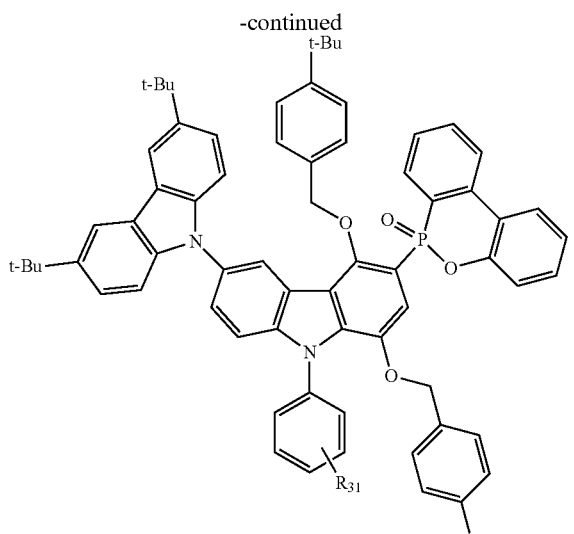
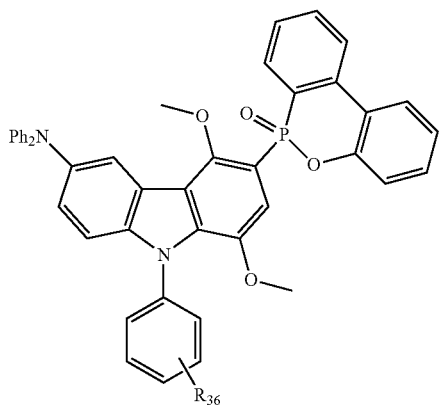
12
-continued
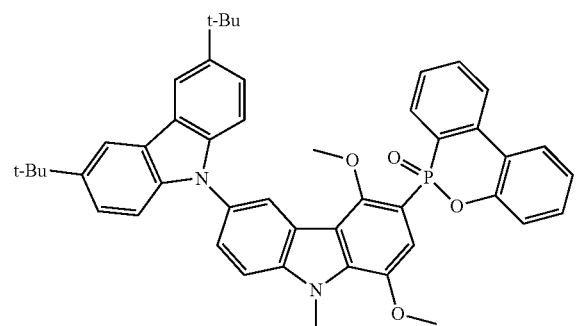
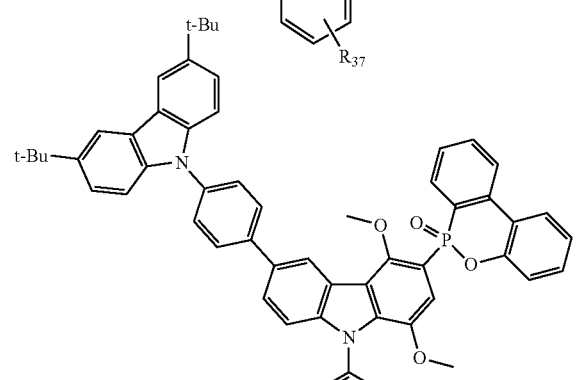
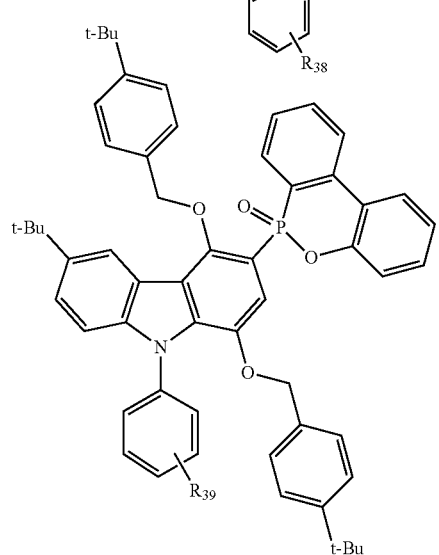

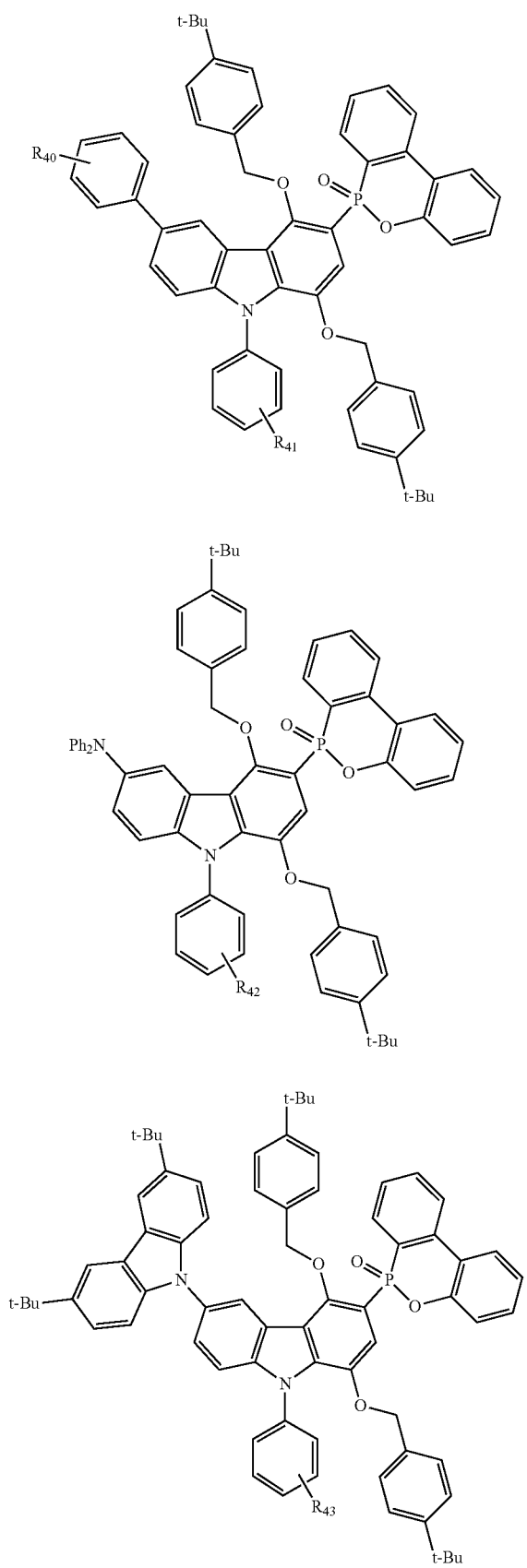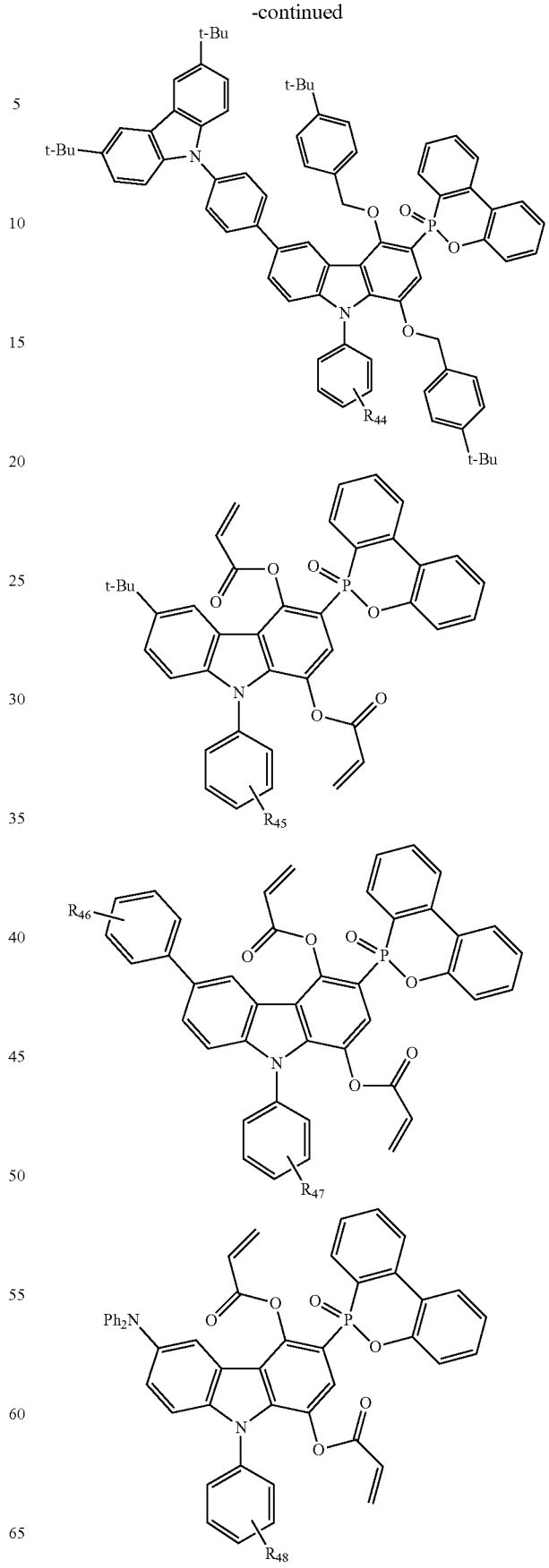

-continued
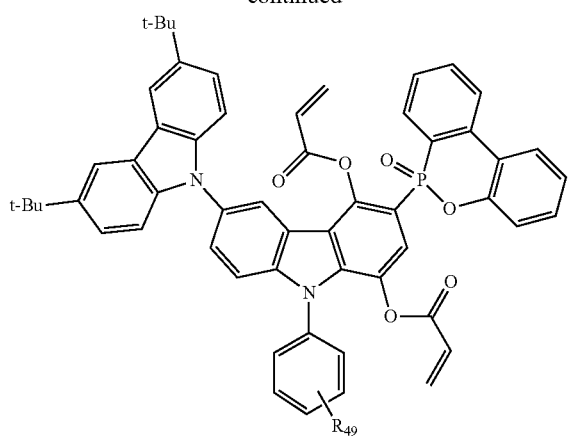
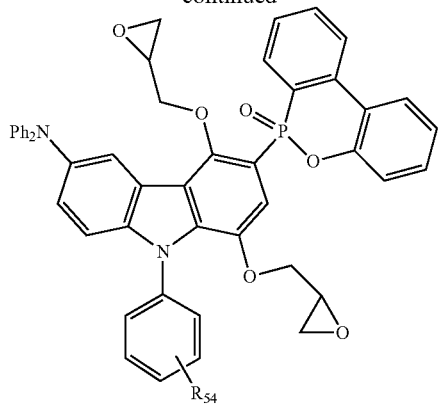
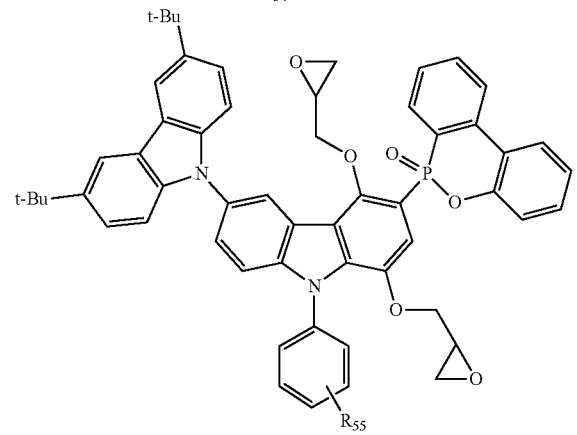
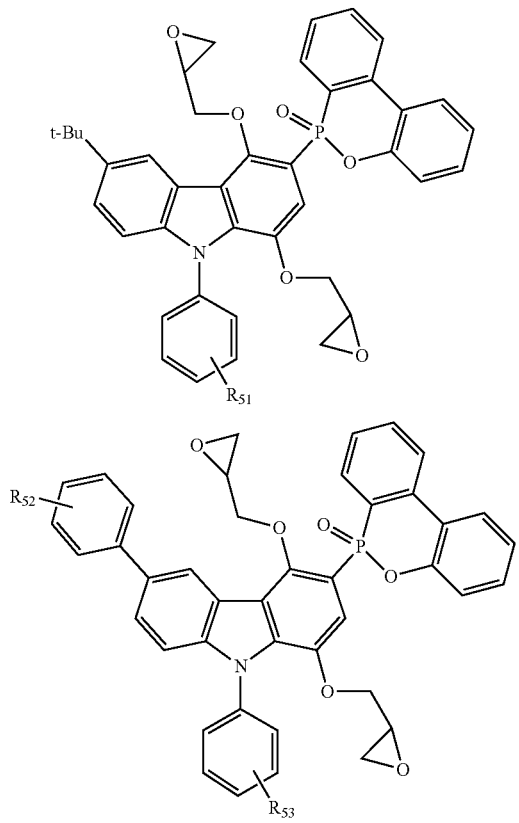
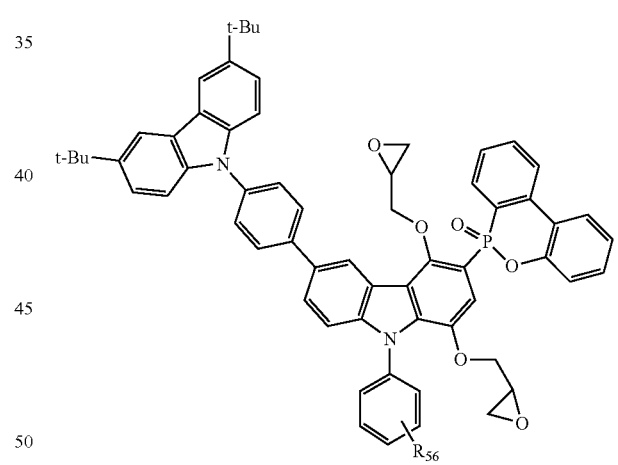

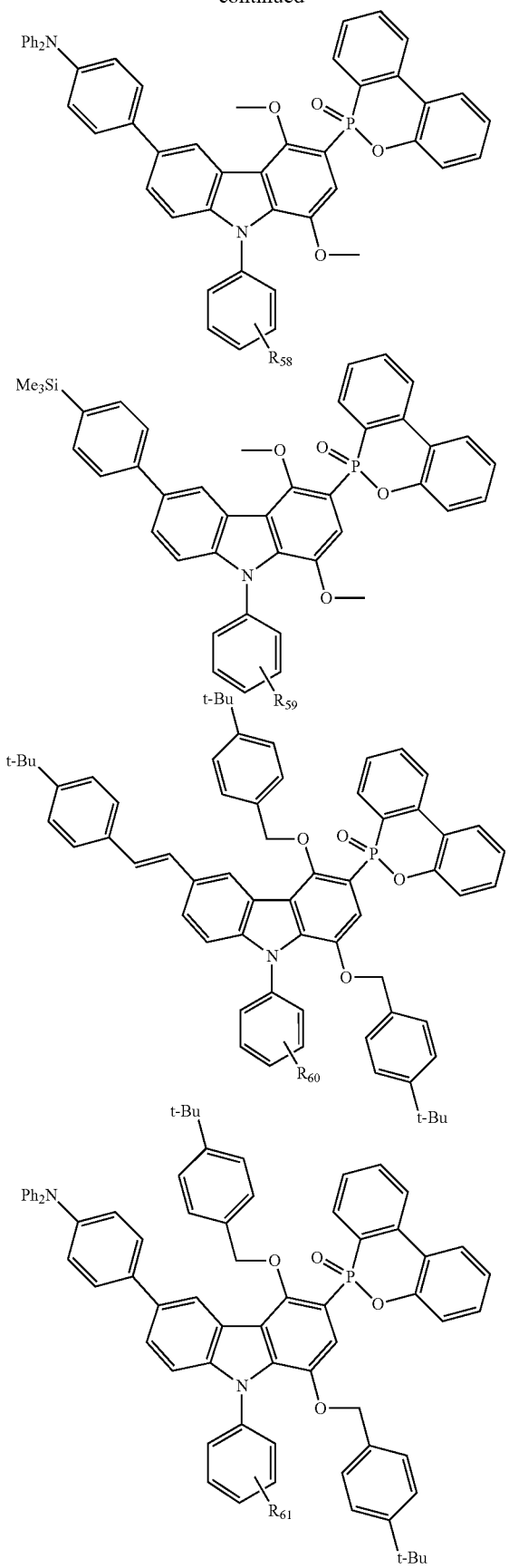
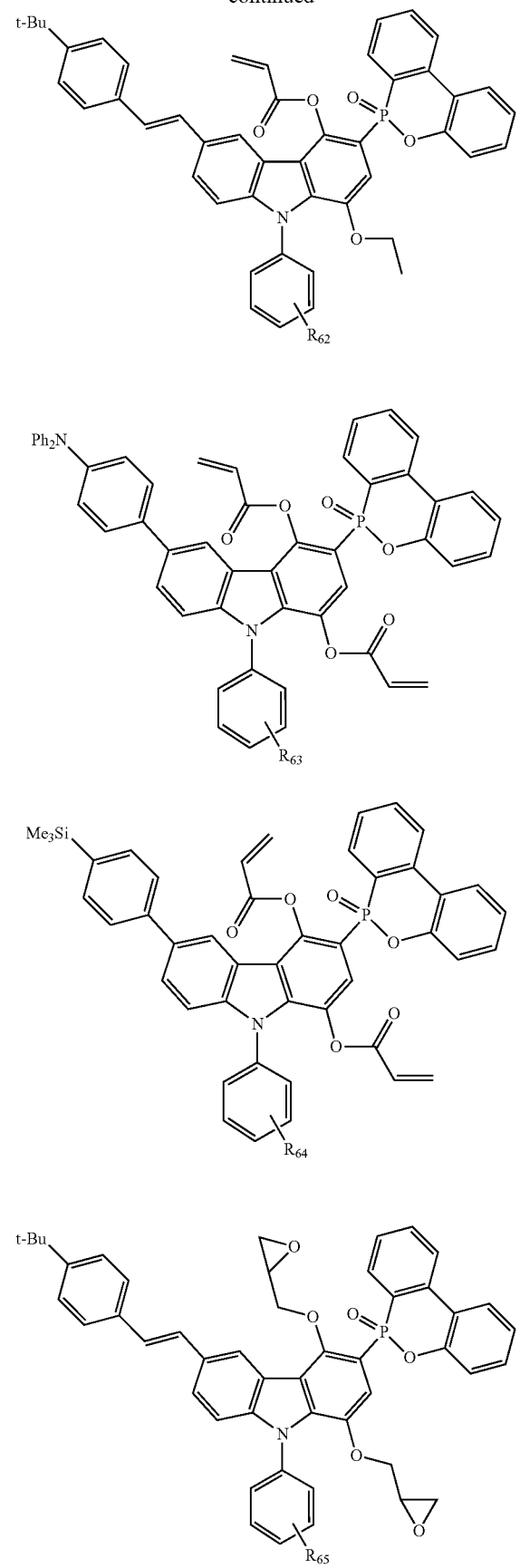

-continued
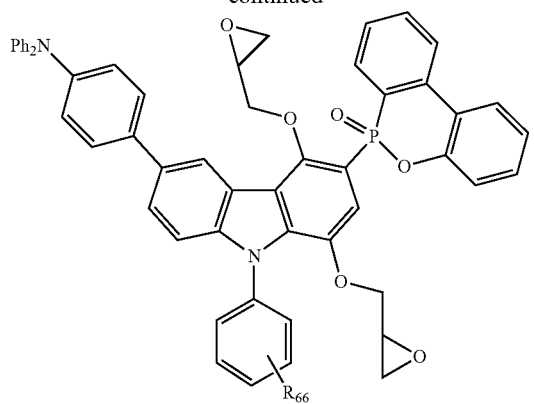
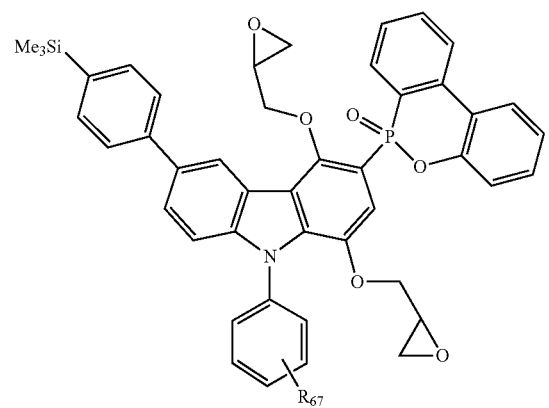
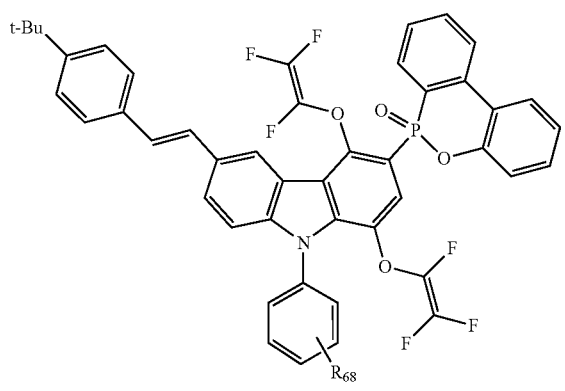
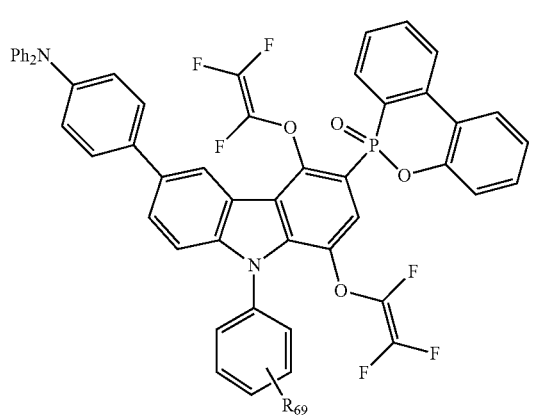
-continued
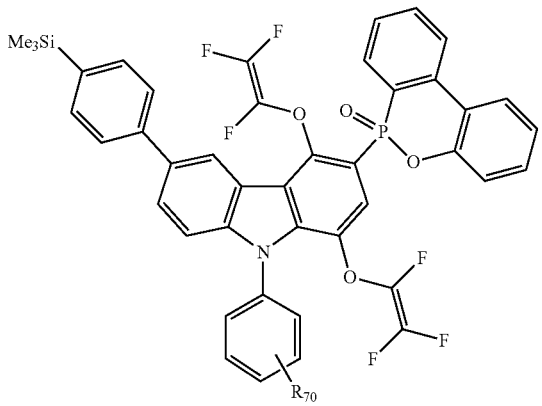
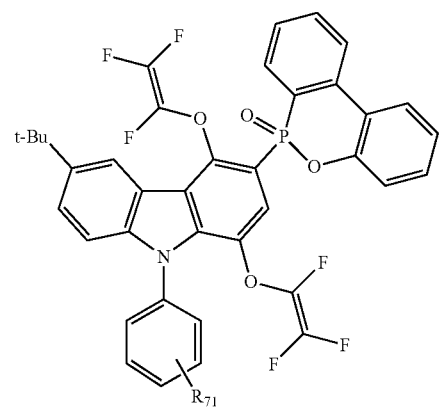
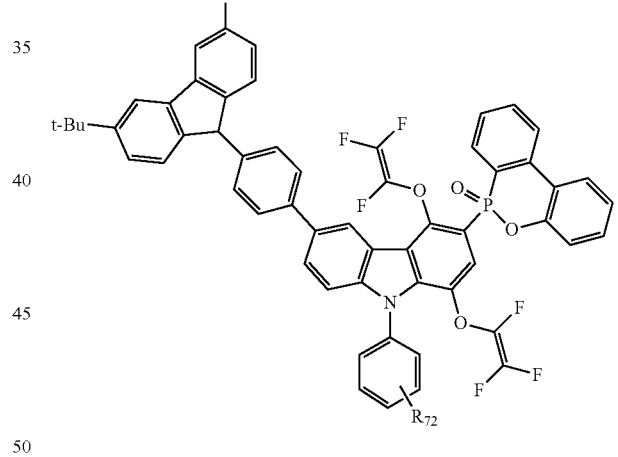
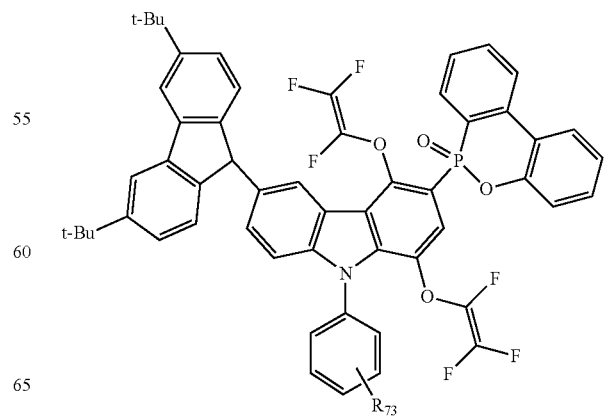

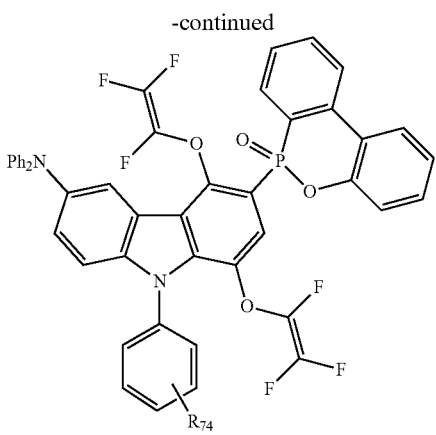

[n and m each may be independently an integer of 0 to 10, $R_{13}$ to $R_{74}$ each may be independently hydrogen, ($C_5$-$C_{30}$) aryl, ($C_3$-$C_{30}$) heteroaryl, ($C_2$-$C_{10}$)alkenyl, ($C_2$-$C_{18}$)alkynyl, straight- or branched-chain ($C_1$-$C_{22}$)alkyl, straight- or branched-chain saturated or unsaturated ($C_1$-$C_{22}$)alkyl containing oxygen, nitrogen, or sulfur, ($C_1$-$C_{22}$)alkoxy, ($C_3$-$C_{22}$)cycloalkyl, ($C_3$-$C_{22}$)cycloalkyl($C_1$-$C_{22}$)alkyl, halogen, cyano, amino, mono- or di-($C_1$-$C_{10}$)alkylamino, mono- or di-($C_6$-$C_{12}$) arylamino, hydroxyl, mono- or di-benzylamino, or mono- or di-($C_3$-$C_{10}$)cycloalkylamino.]

The above-mentioned phosphaphenanthrene-carbazole-based organic light-emitting compound represented by Chemical Formula 1 may be applied to the organic light-emitting device.

Here, the organic light-emitting device may include, for example, a first electrode, a second electrode, and at least one organic layer disposed between the first and second electrodes, wherein at least one of the organic layers may contain the phosphaphenanthrene-carbazole-based organic light-emitting compound. Since this configuration of the organic light-emitting device is only one example, the present invention is not limited thereto.

The organic light-emitting device may have a mono-layer structure in which a single organic layer is provided but may have a multi-layer structure in which at least two layers including a light emitting layer are provided. Here, the organic layer may be formed, for example, by a solution process, which is a wet process and formed by a deposition process, which is a dry process, but the solution process, which is the wet process, may be more preferable. As the wet process, various methods including, for example, a spin coating method, may be used as long as the method may be applied in the art. As the dry process, various methods including, for example, a sputtering method, may be used as long as the method may be applied in the art.

For example, in the case of the multi-layer structure, the organic layer may include at least one layer selected from a group consisting of a hole injection layer; a hole transfer layer; an electron injection layer; an electron transfer layer; and a mixed function layer thereof and the light emitting layer.

As the mixed function layer, for example, there are a layer in which hole transport and light emission are simultaneously performed, a layer in which light emission and electron transport are simultaneously performed, and an electron transport and injection layer.

Particularly, in the present invention, the phosphaphenanthrene-carbazole-based organic light-emitting compound, which is the compound of Chemical Formula 1, may be preferably included in the electron transport layer, the light emitting layer, or light emitting/electron transport layer. As described above, the compound according to the present invention may be preferably used as a light emitting substance or a host material, and the compound may be more preferably used as the host material.

As described above, in the case of using the phosphaphenanthrene-carbazole-based organic light-emitting compound having superior heat resistance and light-emitting properties as the core material of the light-emitting device, in view of light-emitting properties, high efficiency organic light-emitting device may be provided, and a life span of the light-emitting device may be improved.

Meanwhile, hereinafter, a method of manufacturing the phosphaphenanthrene-carbazole-based organic light-emitting compound according to the present invention will be described below. In the case of manufacturing the phosphaphenanthrene-carbazole-based organic light-emitting compound, as long as a final product has the same structure as that in the method described below, any method known in the art may be used as well as the method described below. That is, the present invention is not limited to a solvent, a reaction temperature, a concentration, or a catalyst, a manufacturing yield, or the like, in the method of manufacturing the phosphaphenanthrene-carbazole-based organic light-emitting compound represented by Chemical Formula 1 according to the present invention described below.

Reaction Formula 1 will be described by way of specific example as follows.

In the case of Reaction Formula 1, after bisbenzoquinone and carbazolequinone, which are carbazole precursors, are synthesized from 2,2-hydroxy biphenyl, 9,10-dihdydroxy-9-oxa-10-phosphaphenanthrene-10-oxide is added thereto, thereby making it possible to obtain phosphaphenanthrene-carbazole compound. Then, the desired compound 101 may be obtained by substituting hydroxy with acetyl.

[Reaction Formula 1]

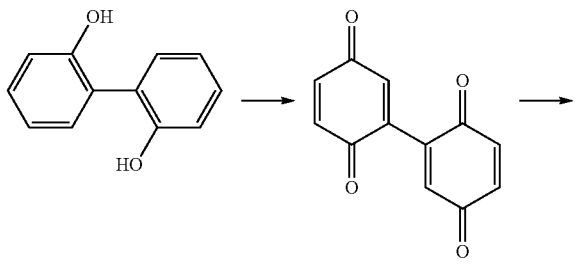

A

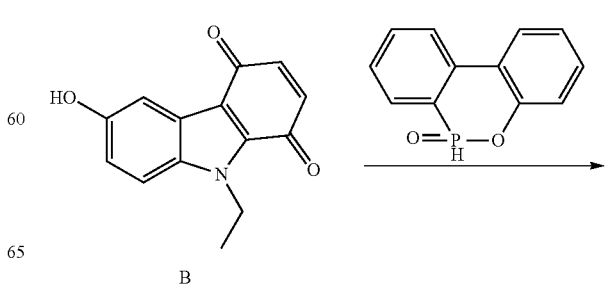

B

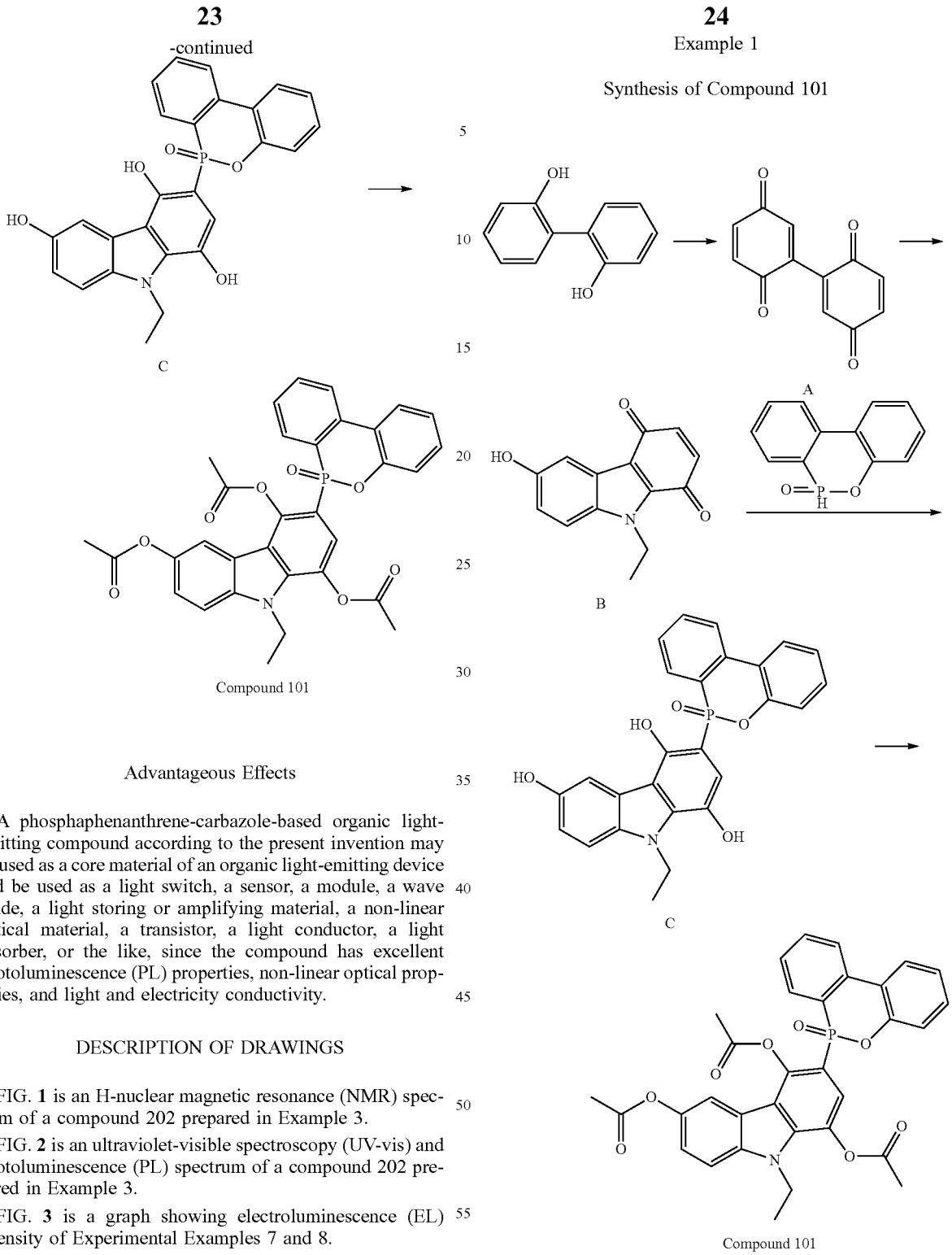

Compound 101

Advantageous Effects

A phosphaphenanthrene-carbazole-based organic light-emitting compound according to the present invention may be used as a core material of an organic light-emitting device and be used as a light switch, a sensor, a module, a wave guide, a light storing or amplifying material, a non-linear optical material, a transistor, a light conductor, a light absorber, or the like, since the compound has excellent photoluminescence (PL) properties, non-linear optical properties, and light and electricity conductivity.

BEST MODEL

Figure 1:
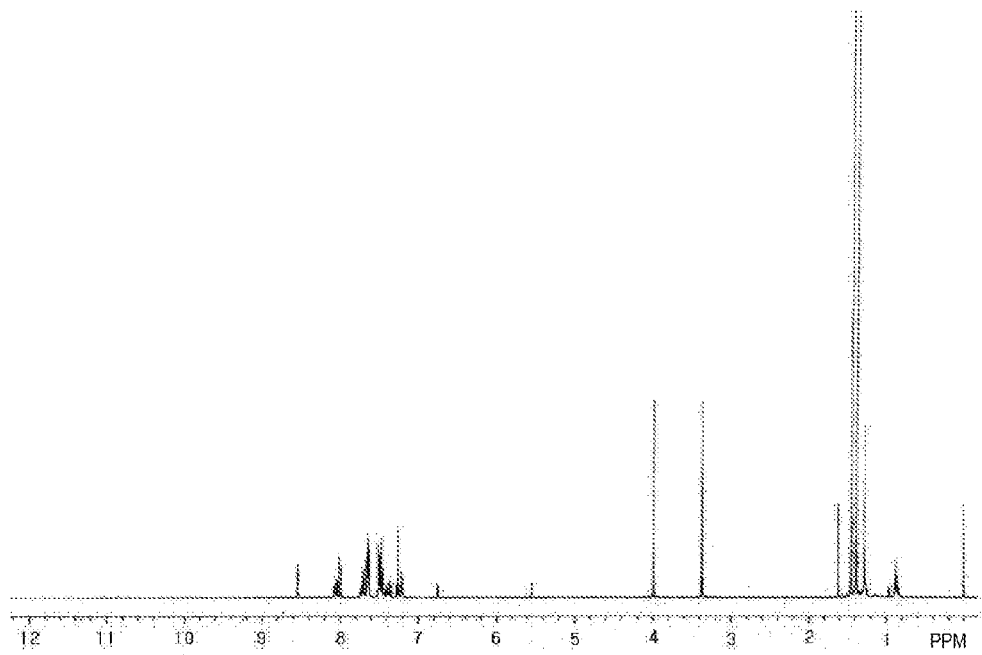
FIG. 1 is an H-nuclear magnetic resonance (NMR) spectrum of a compound 202 prepared in Example 3.
Figure 2:
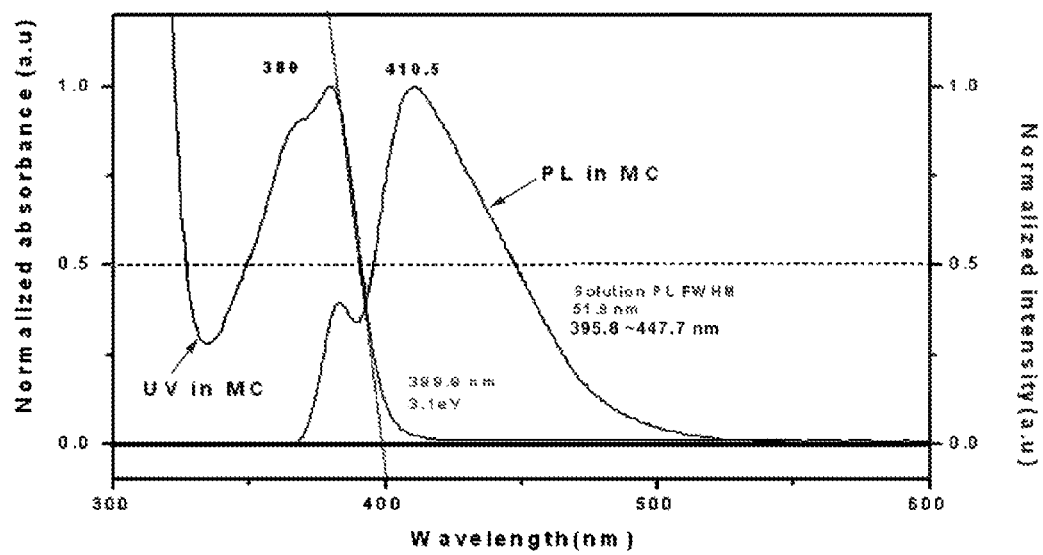
FIG. 2 is an ultraviolet-visible spectroscopy (UV-vis) and photoluminescence (PL) spectrum of a compound 202 prepared in Example 3.
Figure 3:
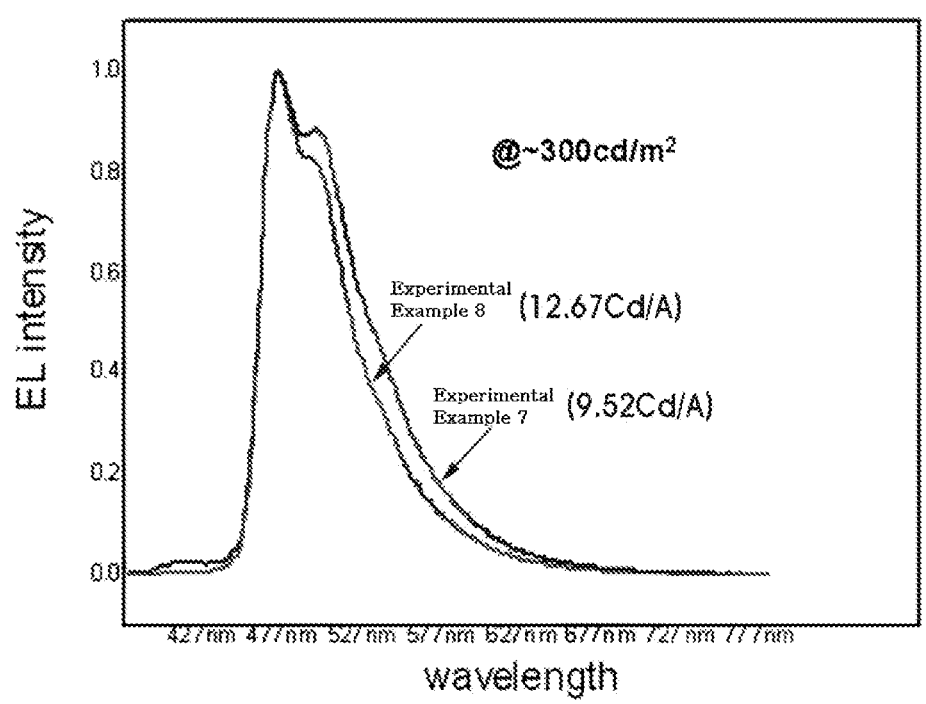
FIG. 3 is a graph showing electroluminescence (EL) intensity of Experimental Examples 7 and 8.

Hereinafter, a method of manufacturing a phosphaphenanthrene-carbazole-based organic light-emitting compound according to the present invention will be described in detail by the Examples. Here, the following Examples are merely illustrations for assisting in the understanding of the present invention, but the present invention is not limited thereto.

Example 1

Synthesis of Compound 101

Compound 101

Synthesis of Bisbenzoquinone (Compound A)

Lead oxide (40.5 g), acetonitrile (260 m), 70% perchloric acid (85 ml) were sequentially input to a 2000 ml two-neck round flask, under argon atmosphere and stirred while lowering a temperature to 0° C. 2,2-hydroxybiphenyl (12.5 g) dissolved in acetonitrile (260 ml) was dropped into the reactor as described above in a state in which the temperature is maintained, followed by stirring for 30 minutes while maintaining the temperature. When the reaction is completed, a reaction catalyst is removed using a filter, and then methylenechloride (340 ml) and brine (340 ml) were input thereto and stirred for 10 minutes. After the obtained solid was filtered and separated, the water layer was extracted with methylenechloride (340 ml). The organic layer was collected, dried over anhydrous magnesium sulfate, and then concentrated under reduced pressure. After concentration, methylenechloride (340 ml) was input to the concentrated organic layer, activated carbon (2.5 g) was added thereto and stirred for 1 hour. Insoluble materials were removed using a celite, and then the filtrate was concentrated under reduced pressure. Isopropyl ether (IPE, 170 ml) was added thereto and stirred so that the solid may be dissolved, followed by filtering and drying, thereby obtaining 3 to 4 g of bisbenzoquinone (Compound A).

$^1$H NMR (CDCl3), δ=6.80-6.90 (t, 3H, aromatic)

Synthesis of Carbazolebenzoquinone (Compound B)

Chloroform (72 ml) and bisbenzoquinone compound (Compound A, 2.03 g) were input to a 500 ml two-neck round bottom flask and dissolved, followed by stirring while lowering a temperature to 0° C. A mixture of 2N ethylamine in methanol solution (4.8 ml) and chloroform (24 ml) were dropped into the stirred solution while maintaining the temperature and stirred for 30 minutes. When the reaction was completed, chloroform (240 ml) was input thereto, and amine was neutralized with 5% hydrochloride. The organic layer was separated from the resultant using water and chloroform and dried over magnesium sulfate. The organic layer was collected, concentrated under reduced pressure, and re-precipitated using hexane, followed by filtering and drying a solid, thereby 1.5 to 2.0 g of carbazolebenzoquinone compound (Compound B).

$^1$H NMR (DMSO, d6), δ=1.25 (d, 3H, CH$_3$), 4.52 (t, 2H, —CH$_2$—N), 6.60 (2s, 2H, aromatic), 6.95 (d, 1H, aromatic), 7.20 (s, 1H, aromatic), 7.48 (d, 1H, aromatic), 9.60 (s, 1H, —OH)

Synthesis of Phosphaphenanthrene-carbazolequinone (Compound C)

Carbazolebenzoquinone (Compound B, 2.9 g), 9,10-dihydroxy-9-oxa-10-phsophaphenanthrene-oxide (3.0 g), and ethoxyethanol (5 ml) were input to a 250 ml one-neck round bottom flask and stirred for 1 hour while maintaining a temperature at 90° C. When the reaction was completed, the solution was concentrated under reduced pressure and purified using a silica gel column. The obtained solid was washed with IPE and dried, thereby obtaining 0.5 g of phosphaphenanthrene-carbazolequinone (Compound C).

Molecular formula (molecular weight): C$_{26}$H$_{20}$NO$_5$P (457.41), UV (THF) lmax: 259 nm, PL (THF) lmax: 320 nm $^1$H NMR (DMSO, d6), δ=1.25 (d, 3H, CH$_3$), 4.52 (t, 2H, —CH$_2$—), 6.25 (d, 1H, aromatic), 6.95 (d, 1H, aromatic), 7.40-7.95 (m, 8H, aromatic), 8.15 (2S, 2H, aromatic), 9.15 (s, 1H, —OH), 9.40 (s, 1H, —OH), 11.0 (s, 1H, —OH)

Synthesis of Acetyl Phosphaphenanthrene-Carbazolequinone (Compound 101)

Phosphaphenanthrene-carbazolequinone (Compound C, 3 g), triethylamine (19 ml), methylchloride (100 ml), and tetrahydrofuran (THF, 20 ml) were input to 250 ml two-neck round bottom flask and stirred while lowering a temperature to 0° C. Acetyl chloride (4.7 ml) was dropped thereinto while maintaining the temperature, and then stirred for 1 hour while maintaining the temperature at 3 to 5° C. When the reaction was completed, the mixture was quenched using saturated ammonium chloride, extracted with methylenechloride, and then washed with brine. The organic layer was dried over magnesium sulfate, concentrated under reduced pressure, and purified using a silica gel column, thereby obtaining 2 g of acetyl phosphaphenanthrene-carbazolequinone compound (Compound 101).

$^1$H NMR (DMSO, d6), δ=1.25 (d, 3H, CH$_3$), 1.87 (s, 3H, CH$_3$), 2.20 (s, 3H, CH$_3$), 2.45 (s, 3H, CH$_3$), 4.55 (d, 2H, CH$_2$), 7.20-7.60 (m, 7H, aromatic), 7.70-7.85 (m, 3H, aromatic), 8.30-8.40 (m, 2H, aromatic)

Example 2

Synthesis of Compound 201

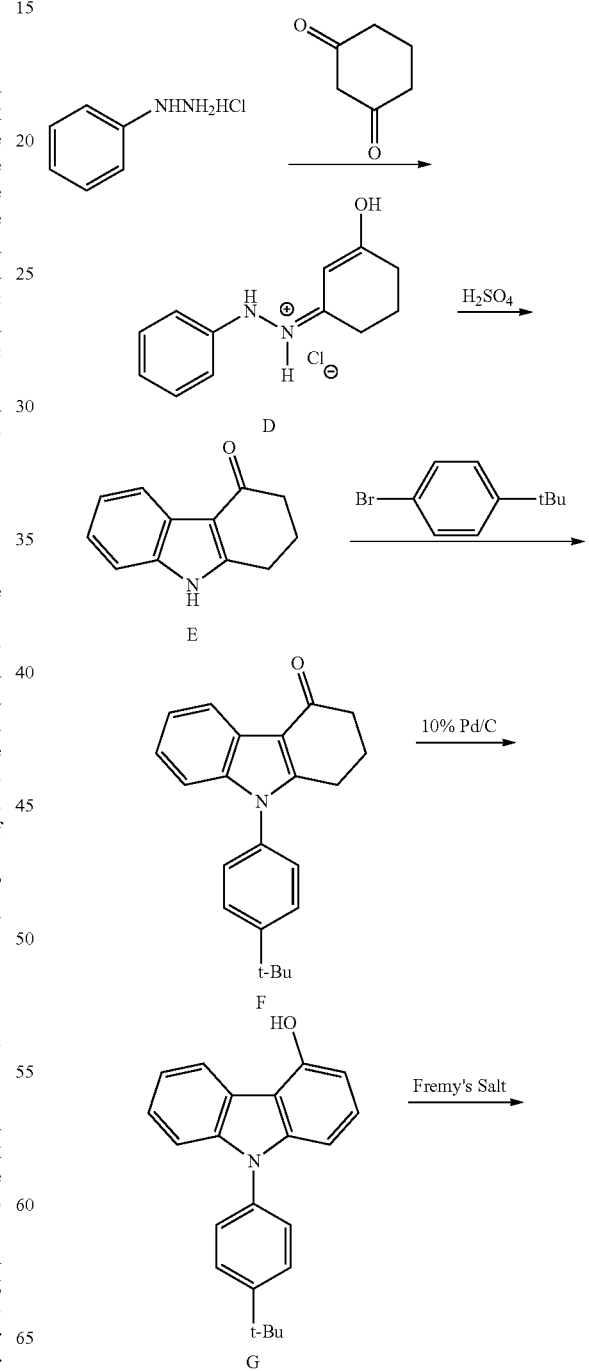

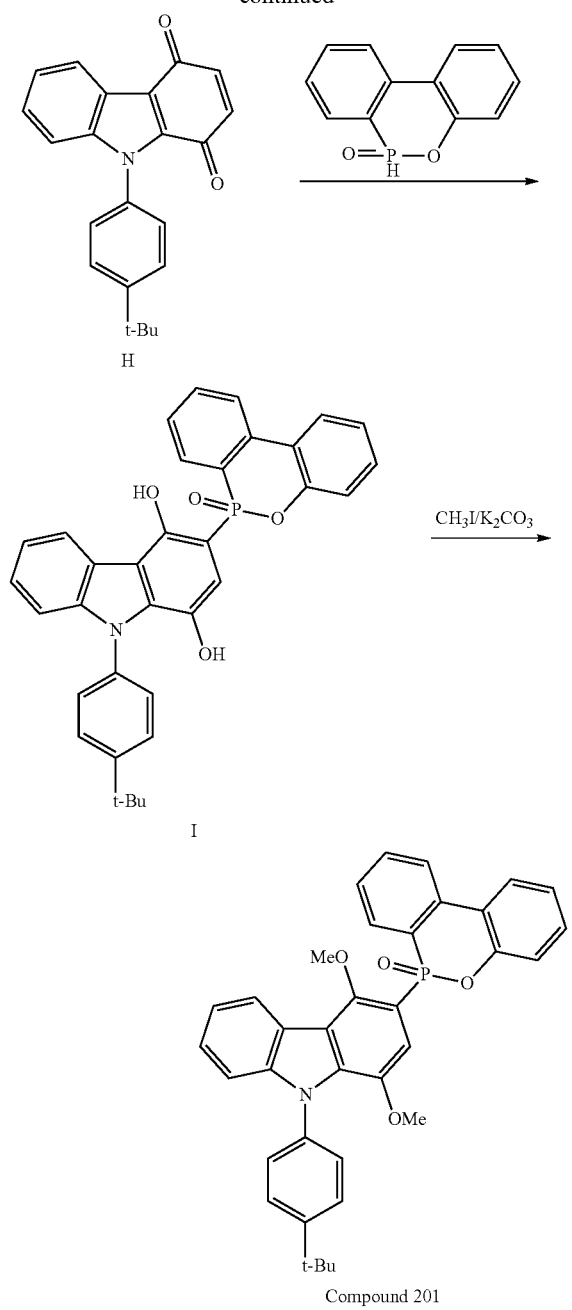

Synthesis of 3-phenylhydrazonecyclohexane-1-on (Compound D)

Phenylhydrazinium chloride (37 g) and 50% acetic acid aqueous solution (74 ml) were mixed with each other and stirred in a 500 ml two-neck round bottom flask. 1,3-cyclohexanedion (28.7 g) was dissolved in 50% acetic acid aqueous solution (23 ml) and slowly added to the stirred solution. The reaction mixture was stirred for 40 minutes while heating the mixture at 50, such that the mixture was dissolved to thereby become a red brown solution. The reaction solution was slowly released at room temperature, and ethylacetate (37 ml) and ethylether (45 ml) were added thereto to crystallize the reaction solution. The crystal product was filtered and washed with IPE, thereby 40 g of 3-phenylhydrazonecyclohexane-1-on (Compound D) as a brown solid.

$^1$H NMR (DMSO-$d_6$) (300 MHz) δ 1.85 (quint, 2H, J=6.0 Hz), 2.43 (t, 2H, J=6.0 Hz), 2.70 (t, 2H, J=6.0 Hz), 5.92 (s, 1H), 6.71-7.19 (m, 5H, ArH), 8.82 (br. s, 1H), 9.03 (br. s, 1H), 11.7 (br. s, 1H)

Synthesis of 1,2,3,4-tetrahydro-9H-carbazole-4-one (Compound E)

In a 1000 ml two-neck round bottom flask, 3-phenylhydrazonecyclohexane-1-one (Compound D, 40 g) and distilled water (370 ml) were mixed, and sulfuric acid (150 ml) was added thereto while filling nitrogen gas. The mixture was stirred for 1.5 hours while maintaining a temperature at 95° C. and cooled to room temperature. The reaction solution was added to distilled water (1200 ml) and stirred for 1 hour in a state in which pH of the solution was set to 3 using 20% NaOH aqueous solution. After the obtained solid was filtered, the wet material was dissolved in THF, dried over magnesium sulfate, and concentrated. IPE was added to the obtained residual and stirred, followed by filtering, thereby obtaining 20 g of 1,2,3,4-tetrahydro-9H-carbazole-4-one (Compound E) as a brown solid.

$^1$H NMR (DMSO-$d_6$) (300 MHz) δ 2.04 (quint, 2H, J=6.3 Hz), 2.35 (t, 2H, J=6.3 Hz), 2.89 (t, 2H, J=6.3 Hz), 7.05 (m, 2H, ArH), 7.31 (m, 1H, ArH), 7.86 (m, 1H, ArH), 11.78 (br. s, 1H, NH).

Synthesis of N-(t-butylphenyl)carbazolone (Compound F)

In a 500 ml two-neck flask, 1,2,3,4-tetrahydro-9H-carbazole-4-one (Compound E, 20 g), t-butyl bromobenzene (60 g), potassium carbonate (43 g), Cu powder (2.1 g), and NMP (70 ml) were mixed and stirred. The reaction mixture was refluxed and stirred for 24 to 30 hours in a state in which the temperature was raised. When the reaction was completed, the reactant was cooled at room temperature, and then the reactant was mixed with ethylacetate (500 ml) and brine (500 ml) and strongly stirred. Floating materials was filtered and removed using celite, and the organic layer was separated. The water layer was extracted using ethylacetate, and the organic layer was collected and dried over magnesium sulfate. The organic layer was concentrated, and the residual was purified using a column chromatography, thereby obtaining 13 g of N-(t-butylphenyl) carbazolone (Compound F).

$^1$H NMR (CDCl3) δ 1.40 (s, 9H), 2.20 (m, 2H), 2.61 (t, 2H), 2.82 (t, 2H), 7.18 (d, 2H, ArH), 7.30 (m, 3H, ArH), 7.56 (d. 2H, ArH), 8.30 (d, 1H, ArH)

Synthesis of N-(t-butylphenyl) hydroxycarbazole (Compound G)

In a 500 ml two-neck flask, N-(t-butylphenyl) carbazolone (Compound F, 13 g) and diphenylether (100 ml) were mixed, and the 10% Pd/C (13 g) was added thereto. This reaction solution was refluxed and stirred for 30 minutes to 1 hour. When the reaction was completed, 80% of diphenylether was removed by distillation under reduced pressure, and a catalyst was removed using celite. The filtrate was washed again with ethylacetate. The filtrate was concentrated under reduced pressure and separated using a column chromatography, thereby obtaining 11 g of N-(t-butylphenyl)hydroxycarbazole (Compound G).

$^1$H NMR (CDCl3) δ 1.41 (s, 9H), 5.44 (s, 1H, OH), 6.60 (d, 1H, ArH), 7.00 (d, 1H, ArH), 7.22 (t, 1H, ArH), 7.30 (t, 1H, ArH), 7.38 (t, 2H, ArH), 7.45 (d, 2H, ArH), 7.57 (d, 2H, ArH), 8.34 (d, 1H, ArH)

Synthesis of N-(t-butylphenyl)carbazolequinone (Compound H)

In a 100 ml two-neck flask, N-(t-butylphenyl)hydroxycarbazole (Compound G, 3.15 g), acetone (400 ml), and distilled water (400 ml) were mixed, and potassium dihydrogen phosphate (1.36 g) was added thereto and stirred. Potassium nitrosodisulfonate (10.73 g) was added thereto while stirring the mixture at room temperature. After stirring for 3 hours while maintaining room temperature, when the reaction was completed, acetone was removed by distillation under reduced pressure. The resultant was extracted with methylenechloride, and the organic layer is dried over anhydrous magnesium sulfate and concentrated under reduced pressure, thereby obtaining 2.5 g of black-red N-(t-butylphenyl)carbazolequinone (Compound H).

$^1$H NMR (CDCl3) δ 1.41 (s, 9H), 6.18 (d, 1H, quinone-H), 7.13 (d, 1H, quinone-H), 7.20-7.38 (m, 5H, ArH), 7.63 (d, 2H, ArH), 8.23 (d, 1H, ArH)

Synthesis of N-(t-butylphenyl)dihydroxy carbazole phosphaphenanthrene (Compound I)

In a 250 ml two-neck flask, N-(t-butylphenyl)carbazolequinone (Compound H, 7.0 g), 9,10-dihydroxy-9-oxa-10-phosphaphenanthrene-10-oxide (4.6 g), and 2-ethoxyethanol (20 ml) were mixed and stirred. This reaction solution was stirred for 30 minutes to 1 hour while raising a temperature to 90 to 100° C. When the reaction is completed, the resultant was cooled to room temperature and precipitated by inputting methanol (200 ml). The produced solid was filtered, and the filtrate was concentrated and solidified using methanol, thereby obtaining 4.0 g of N-(t-butylphenyl) dihydroxy carbazole phosphaphenanthrene (Compound I).

$^1$H NMR (DMSO-d$_6$) δ 1.41 (s, 9H), 7.18-7.21 (m, 3H, ArH), 7.35-7.46 (m, 6H, ArH), 7.60-7.75 (m, 4H, ArH), 7.96-8.07 (m, 3H, ArH), 8.31 (d, 1H, ArH), 8.52 (s, 1H, OH), 9.40 (s, 1H, OH)

Synthesis of N-(t-butylphenyl)dimethoxy carbazole phosphaphenanthrene (Compound 201)

In a 250 ml two-neck flask, N-(t-butylphenyl)dihydroxy carbazole phosphaphenanthrene (Compound I, 4.12 g), potassium carbonate (21 g), and acetone (100 ml) were mixed and stirred. Methyliodide (17.4 g) was added thereto, followed by refluxing and stirring for 1 hour. The reaction solution was filtered, and the filtrate was concentrated and dissolved in ethylacetate. The resultant was washed with distilled water, and the organic layer was dried over anhydrous magnesium sulfate. The dried organic layer was concentrated by distillation under reduced pressure and purified using a column chromatography, thereby obtaining 2 g of N-(t-butylphenyl)dimethoxy carbazole phosphaphenanthrene (Compound 201).

$^1$H NMR (DMSO-d$_6$) δ 1.41 (s, 9H), 3.36 (s, 3H), 3.99 (s, 3H), 7.18-7.21 (m, 3H, ArH), 7.35-7.46 (m, 6H, ArH), 7.60-7.75 (m, 4H, ArH), 7.96-8.07 (m, 3H, ArH), 8.31 (d, 1H, ArH)

Example 3

Synthesis of Compound 202

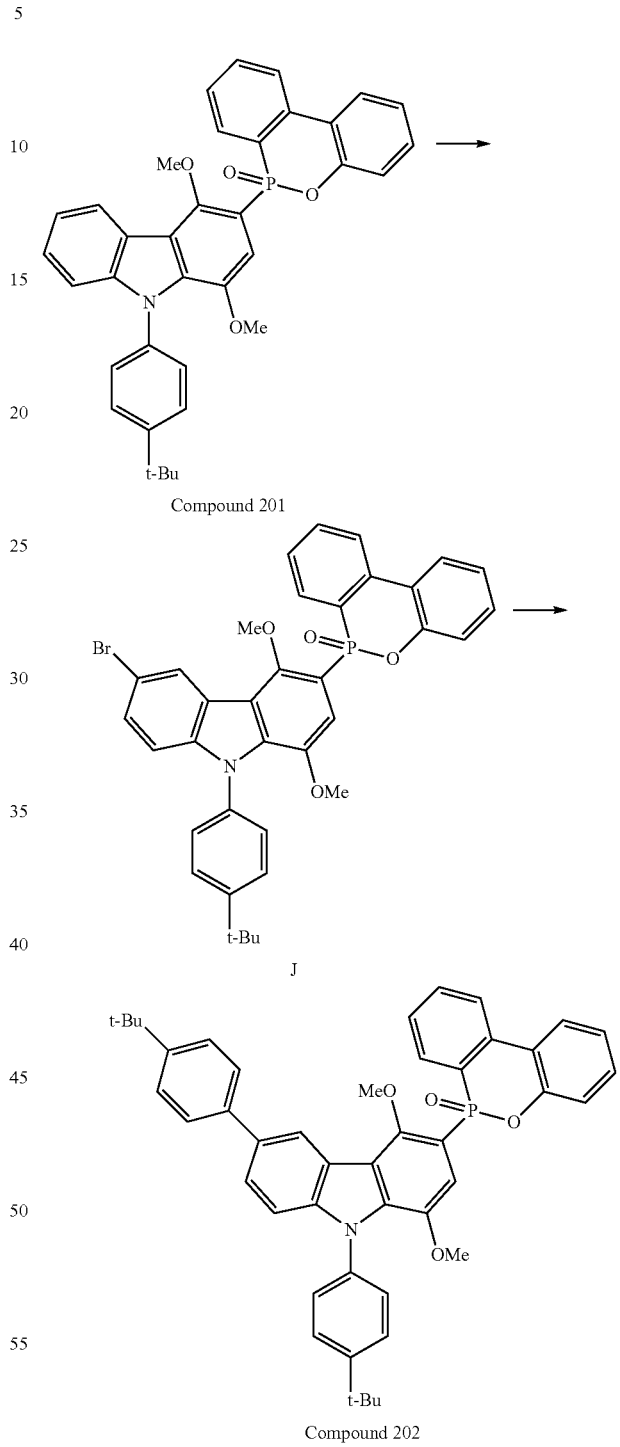

Synthesis of N-(t-butylphenyl)dimethoxy bromo carbazole phosphaphenanthrene (Compound J)

In a 250 ml two-neck flask, N-(t-butylphenyl)dimethoxy carbazole phosphaphenanthrene (Compound 201, 3 g) and methylenechloride (30 ml) were mixed and dissolved, and then the temperature was lowered to 10° C. or less. N-bromosuccinimide (1.0 g) was slowly added thereto while maintaining the temperature at 10° C. or less. When addition of N-bromosuccinimide (1.0 g) was completed, the temperature was slowly raised to room temperature, followed by stirring 2 hours. When the reaction was completed, the reaction solution was concentrated, and methanol (50 ml) was input thereto, followed by stirring and filtration, thereby obtaining 3.2 g of N-(t-butylphenyl)dimethoxy bromo carbazole phosphaphenanthrene (Compound J).

$^1$H NMR (CDCl$_3$) δ 1.41 (s, 9H), 3.36 (s, 3H), 3.99 (s, 3H), 7.08-7.75 (m, 12H, ArH), 7.95-8.06 (m, 3H, ArH), 8.23 (1, 1H, ArH)

Synthesis of N-(t-butylphenyl)dimethoxy t-butylphenyl carbazole phosphaphenanthrene (Compound 202)

In a 250 ml two-neck flask, N-(t-butylphenyl)dimethoxy bromo carbazole phosphaphenanthrene (Compound J, 6.3 g), 4-t-butylphenylboronic acid (2.6 g), tetrabutyl ammonium bromide (0.3 g), 2M potassium carbonate aqueous solution (60 ml), toluene 60 ml, and tetrahydrofuran (20 ml) were mixed and strongly stirred.

Tetrakis(triphenylphosphine)palladium (1.1 g) was input to this stirred solution, followed by refluxing and stirring for 3 hours. When the reaction is completed, the mixture was cooled to room temperature, and layers were separated and extracted using methylenechloride. The organic layer was dried over anhydrous magnesium sulfate and concentrated. 4 g of N-(t-butylphenyl)dimethoxy t-butylphenyl carbazole phosphaphenanthrene (Compound 202) was obtained using a column chromatography.

$^1$H NMR (CDCl$_3$) δ 1.39 (s, 9H), 1.41 (s, 9H), 3.38 (s, 3H), 3.99 (s, 3H), 7.09-7.75 (m, 16H, ArH), 7.95-8.06 (m, 3H, ArH), 8.27 (1, 1H, ArH)

Example 4

Synthesis of Compound 301

-continued

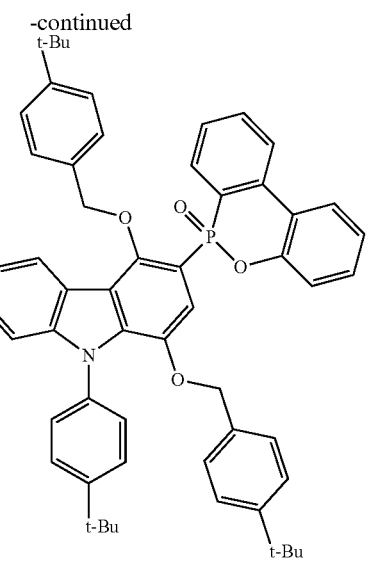

Compound 301

In a 250 ml two-neck flask, N-(t-butylphenyl)dihydroxy carbazole phosphaphenanthrene (Compound I, 5 g), potassium carbonate (3.7 g), and acetone (100 ml) were mixed and stirred. 4-t-butylbenzylbromide (5 g) was added thereto, followed by refluxing and stirring for 1 hour. The reaction solution was filtered, and the filtrate was concentrated and dissolved in ethylacetate. The resultant was washed with distilled water, and the organic layer was dried over anhydrous magnesium sulfate. The dried organic layer was concentrated by distillation under reduced pressure and purified using a column chromatography, thereby obtaining 5.5 g of N-(t-butylphenyl)di-(t-butylbenzyloxy) carbazole phosphaphenanthrene (Compound 301).

$^1$H NMR (CDCl$_3$) δ 1.36 (s, 18H), 1.42 (s, 9H), 6.63 (d, 2H), 6.99 (d, 2H), 7.15-7.71 (m, 23H, ArH), 8.10 (d, 1H, ArH), 8.28 (d, 1H, ArH).

Example 5

Synthesis of Compound 302

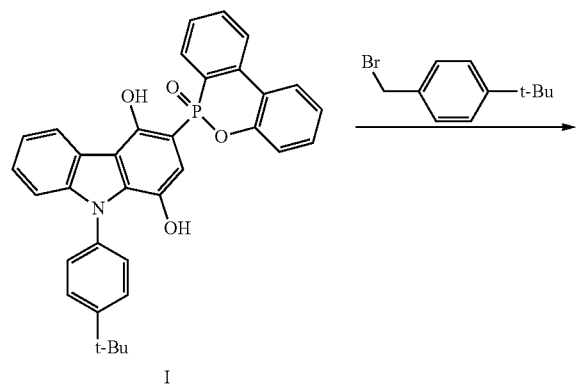

I

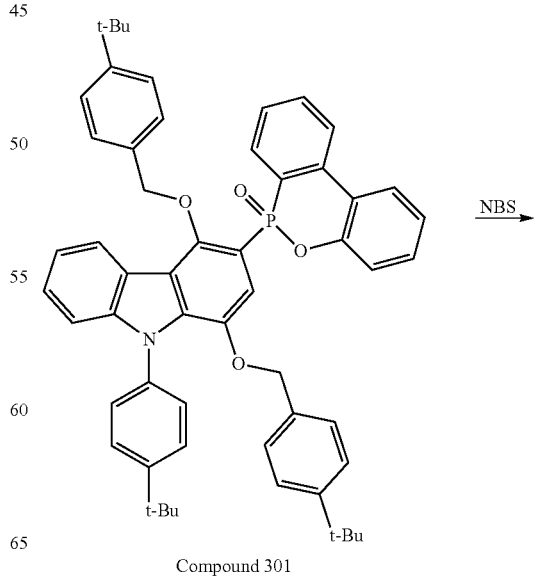

Compound 301

-continued

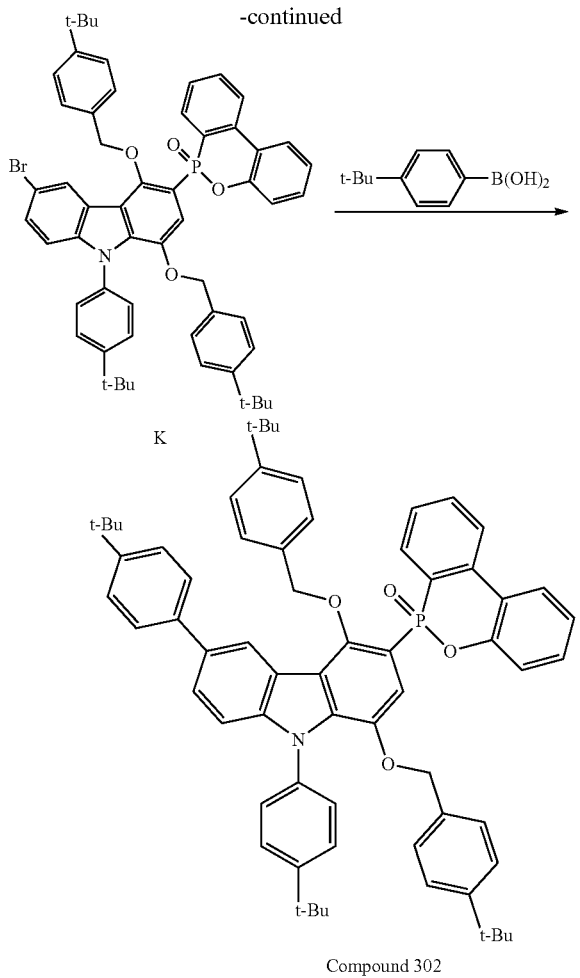

Compound 302

Synthesis of N-(t-butylphenyl)di-(t-butylbenzyloxy) bromo carbazole phosphaphenanthrene (Compound K)

In a 250 ml two-neck flask, N-(t-butylphenyl)di-(t-butylbenzyloxy) carbazole phosphaphenanthrene (Compound 301, 5.2 g) and methylenechloride (50 ml) were mixed and dissolved. This solution was cooled at 10° C. or less, and N-bromosuccinimide (1.2 g) was slowly input thereto while maintaining the temperature. The mixture was stirred for 2 hours while slowly raising the temperature. When the reaction was completed, the reaction solution was concentrated and purified using a column chromatography, thereby obtaining 4.0 g of N-(t-butylphenyl)di-(t-butylbenzyloxy) bromo carbazole phosphaphenanthrene (Compound K).

$^1$H NMR (CDCl$_3$) δ 1.36 (s, 18H), 1.42 (s, 9H), 6.63 (d, 2H), 6.99 (d, 2H), 7.15-7.71 (m, 22H, ArH), 8.10 (d, 1H, ArH), 8.28 (s, 1H, ArH)

Synthesis of N-(t-butylphenyl)di-(t-butylbenzyloxy) t-butylphenyl carbazole phosphaphenanthrene (Compound 302)

In a 250 ml two-neck flask, N-(t-butylphenyl)di-(t-butylbenzyloxy) bromo carbazole phosphaphenanthrene (Compound K, 4.0 g), 4-t-butylphenylboronic acid (1.2 g), tetra-butyl ammonium bromide (0.14 g), 2M potassium carbonate aqueous solution (40 ml), toluene 40 ml, and tetrahydrofuran (15 ml) were mixed and strongly stirred. Tetrakis(triphenylphosphine)palladium (0.5 g) was input to this stirred solution, followed by refluxing and stirring for 3 hours. When the reaction was completed, the resultant was cooled to room temperature, and then layers were separated and extracted. The obtained organic layer was dried over anhydrous magnesium sulfate and concentrated. After the concentrated solution was dissolved in a small amount of tetrahydrofuran, methanol was dropped thereinto, followed by re-precipitation and purification using a short column, thereby obtaining 2.3 g of N-(t-butylphenyl)di-(t-butylbenzyloxy) t-butylphenyl carbazole phosphaphenanthrene (Compound 302).

$^1$H NMR (CDCl$_3$) δ 1.36 (s, 18H), 1.38 (s, 9H), 1.42 (s, 9H), 6.75 (d, 2H), 7.02 (d, 2H), 7.10-7.75 (m, 26H, ArH), 8.10 (d, 1H, ArH), 8.60 (s, 1H, ArH)

Experimental Example 1

Ultraviolet-Visible Spectroscopy (UV-Vis) and Photoluminescence (PL) Test

UV-vis and photoluminescence (hereinafter, referred to as PL) values with respect to the compounds synthesized in the Examples were measured and shown in Table 1. The UV-vis was measured using a Varian Cary5000 UV/Vis spectrophotometer, and PL was measured using LS55 luminescence spectro-photometer luminescence (Perkin Elimer). Test samples were prepared using tetrahydrofuran solution, UV-vis spectra of the test samples were measured, and PL properties were measured at a wavelength at which UV-vis peak maximally appears.

TABLE 1

| | Structure and UV/PL data of compounds | | | |
|---|---|---|---|---|
| Compound | Structural Formula | Molecular formula (molecular weight) | UV(THF) Imax(nm) | PL(THF) Imax(nm) |
| 101 | | C$_{32}$H$_{26}$NO$_8$P (583.52) | 247 nm | 366 nm |

TABLE 1-continued

Structure and UV/PL data of compounds

| Compound | Structural Formula | Molecular formula (molecular weight) | UV(THF) Imax(nm) | PL(THF) Imax(nm) |
|---|---|---|---|---|
| 201 | (structure with carbazole, MeO, OMe, P=O dibenzofuran-like, N-phenyl-t-Bu) | $C_{36}H_{32}NO_4P$ (573.62) | 250 nm | 395 nm |
| 202 | (structure with carbazole substituted with 4-t-Bu-phenyl, MeO, OMe, P=O group, N-phenyl-t-Bu) | $C_{46}H_{44}NO_4P$ (705.82) | 380 nm | 410.5 nm |

Experimental Example 2

Electroluminescence Test

ITO/PEDOT/Compound 201+Firpic were formed by a solution process, and TPBI/LiF/Al was formed by a deposition process, such that a device structure of ITO/PEDOT/Compound 201+Firpic/TPBI/LiF/Al was configured. Then, the electroluminescence test was performed. As a result, the device showed maximum efficiency of 3.3 Cd/A with CIE coordinates of (0.17, 0.35).

Experimental Example 3

Electroluminescence Test

ITO/PEDOT/Compound 201+Firpic were formed by a solution process, and Balq/LiF/Al was formed by a deposition process, such that a device structure of ITO/PEDOT/Compound 201+Firpic/Balq/LiF/Al was configured. Then, an electroluminescence test was performed. As a result, the device showed the maximum efficiency of 3.6 Cd/A with CIE coordinates of (0.17, 0.33).

Experimental Example 4

Electroluminescence Test

NPB/Compound 201+Firpic were formed by a solution process, and Balq/LiF/Al was formed by a deposition process, such that a device structure of NPB/Compound 201+Firpic/Balq/LiF/Al was configured. Then, an electroluminescence test was performed. As a result, the device showed a maximum efficiency of 0.75 Cd/A with CIE coordinates of (0.17, 0.28).

Experimental Example 5

Electroluminescence Test

ITO/PEDOT/Compound 202+Firpic were formed by a solution process, and Balq/LiF/Al was formed by a deposition process, such that a device structure of ITO/PEDOT/Compound 202+Firpic/Balq/LiF/Al was configured. Then, an electroluminescence test was performed. As a result, the device showed a maximum efficiency of 3.4 Cd/A with CIE coordinates of (0.18, 0.33).

Experimental Example 6

Electroluminescence Test

NPB/compound 202+Firpic were formed by a deposition process, and Balq/LiF/Al was formed by a deposition process, such that a device structure of NPB/compound 202+Firpic/Balq/LiF/Al was configured. Then, an electroluminescence test was performed. As a result, the device showed the maximum efficiency of 5.66 Cd/A with CIE coordinates of (0.16, 0.33).

Experimental Example 7

Electroluminescence Test

PEDOT:PSS/PVK/Compound 202+Firpic were formed by a solution process, and TPBI/BaF2/Al was formed by a deposition process, such that a device structure of PEDOT:PSS/PVK/Compound 202+Firpic/TPBI/BaF2/Al was configured. Then, an electroluminescence test was performed. As a result, the device showed the maximum efficiency of 9.52 Cd/A with CIE coordinates of (0.18, 0.38).

Experimental Example 8

Electroluminescence Test

PEDOT:PSS:PFI/PVK/Compound 202+Firpic were formed by a solution process, and TPBI/BaF2/Al were formed by a deposition process, such that a device structure of PEDOT:PSS:PFI/PVK/Compound 202+Firpic/TPBI/BaF2/Al was configured. Then, an electroluminescence test was performed. As a result, the device showed the maximum current efficiency of 12.67 Cd/A with CIE coordinates of (0.17, 0.36).

TABLE 2

| classification | Deposition process | | Solution process | |
|---|---|---|---|---|
| | Efficiency (Cd/A) | CIE (x, y) | Efficiency (Cd/A) | CIE (x, y) |
| Compound 201 | 0.75 | 0.17, 0.28 | 3.6 | 0.17, 0.33 |
| Compound 202 | 5.66 | 0.16, 0.33 | 3.4 | 0.18, 0.33 |

As shown in Experimental Examples, a Compound 201+Firpic layer or a Compound 202+Firpic layer may be formed by the deposition process or the solution process, but it may be appreciated that in the case in which the solution process was applied, excellent test results were obtained as shown in Table 2 in which the solution process and the deposition process were compared with each other.

The invention claimed is:

1. A phosphaphenanthrene-carbazole-based organic light-emitting compound represented by the following Chemical Formula 1:

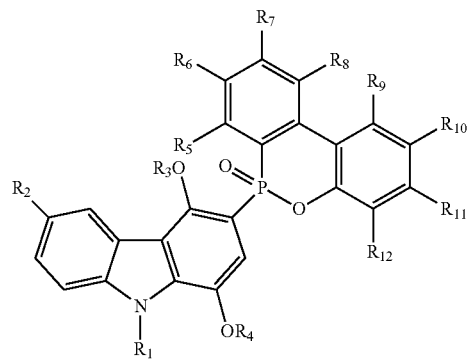

Chemical Formula 1 in Chemical Formula 1, $R_1$ is hydrogen, $(C_1-C_{30})$alkyl, $(C_6-C_{30})$aryl, $(C_3-C_{30})$heteroaryl, $(C_2-C_{10})$alkenyl, $(C_2-C_{18})$alkynyl, amino, mono- or di$(C_1-C_{30})$alkylamino, or mono- or di$(C_6-C_{30})$arylamino;

$R_2$ is hydrogen, hydroxyl, $(C_1-C_{30})$alkyl, $(C_6-C_{30})$aryl, $(C_3-C_{30})$heteroaryl, N-carbazolyl, $(C_2-C_{10})$alkenyl, $(C_2-C_{18})$alkynyl, $(C_6-C_{30})$aryloxy, $(C_1-C_{18})$alkyloxy, $(C_1-C_{30})$alkylcarbonyloxy, amino, mono- or di$(C_1-C_{30})$alkylamino, or mono- or di$(C_6-C_{30})$arylamino;

$R_3$ and $R_4$ each are independently hydrogen, $(C_1-C_{30})$alkyl, $(C_6-C_{30})$aryl, $(C_3-C_{30})$heteroaryl, $(C_6-C_{30})$ar$(C_1-C_{30})$alkyl, $(C_2-C_{10})$alkenyl, $(C_2-C_{18})$alkynyl$(C_1-C_{30})$alkylcarbonyl, $(C_2-C_{10})$alkenylcarbonyl, amino, mono- or di$(C_1-C_{30})$alkylamino, or mono- or di$(C_6-C_{30})$arylamino;

$R_5$ to $R_{12}$ are the same as or different from each other, each independently, and independently hydrogen, straight- or branched-chain $(C_1-C_{30})$alkyl, straight- or branched-chain $(C_1-C_{30})$alkyl including oxygen, nitrogen or sulfur, $(C_1-C_{30})$alkoxy, $(C_3-C_{30})$cycloalkyl, $(C_3-C_{30})$cycloalkyl$(C_1-C_{30})$alkyl, $(C_6-C_{30})$aryl, halogen, cyano, amino, mono- or di$(C_1-C_{30})$alkylamino, mono- or di$(C_6-C_{30})$arylamino, hydroxy, nitro, mono- or di-benzylamino, or $(C_3-C_{30})$cycloalkylamino; and aryl, heteroaryl, alkenyl, alkynyl, or amino of $R_1$, aryl, heteroaryl, N-carbazolyl, alkenyl, alkynyl, aryloxy, alkyloxy, or amino of $R_2$, and alkyl, aryl, heteroaryl, aralkyl, alkenyl, alkynyl, or amino of $R_3$ and $R_4$ may be further substituted with at least one selected from straight- or branched-chain $(C_1-C_{30})$alkyl substituted or unsubstituted with halogen, $(C_3-C_{30})$cycloalkyl, $(C_3-C_{30})$cycloalkyl$(C_1-C_{30})$alkyl, $(C_2-C_{10})$alkenyl, $(C_2-C_{10})$alkynyl, $(C_6-C_{30})$aryl, straight- or branched chain $(C_1-C_{30})$alkyl including oxygen, nitrogen or sulfur, $(C_1-C_{30})$alkoxy, $(C_3-C_{30})$heteroaryl, N-carbazolyl, 3- to 7-membered heterocycloalkyl including at least one of oxygen, nitrogen or sulfur in the hetero ring, cyano, halogen, 9-oxa-10-phosphaphenathrene-10-oxide, $(C_6-C_{30})$aryloxy, $(C_6-C_{30})$arylsulfonyl, amino, mono- or di$(C_1-C_{30})$alkylamino, mono- or di$(C_6-C_{30})$arylamino, mono- or di-benzyl, mono- or di$(C_3-C_{30})$cycloalkylamino, hydroxyl, nitro, $(C_2-C_7)$alkenyloxy, $(C_2-C_7)$alkynyloxy, $(C_2-C_7)$alkenylcarbonyloxy, $(C_2-C_7)$alkynylcarbonyloxy, tri$(C_1-C_{30})$alkylsilyl, di$(C_1-C_{30})$alkyl$(C_6-C_{30})$arylsilyl, di$(C_6-C_{30})$ar$(C_1-C_{30})$alkylsilyl, and tri$(C_6-C_{30})$arylsilyl.

2. A phosphaphenanthrene-carbazole-based organic light-emitting compound selected from the following compounds

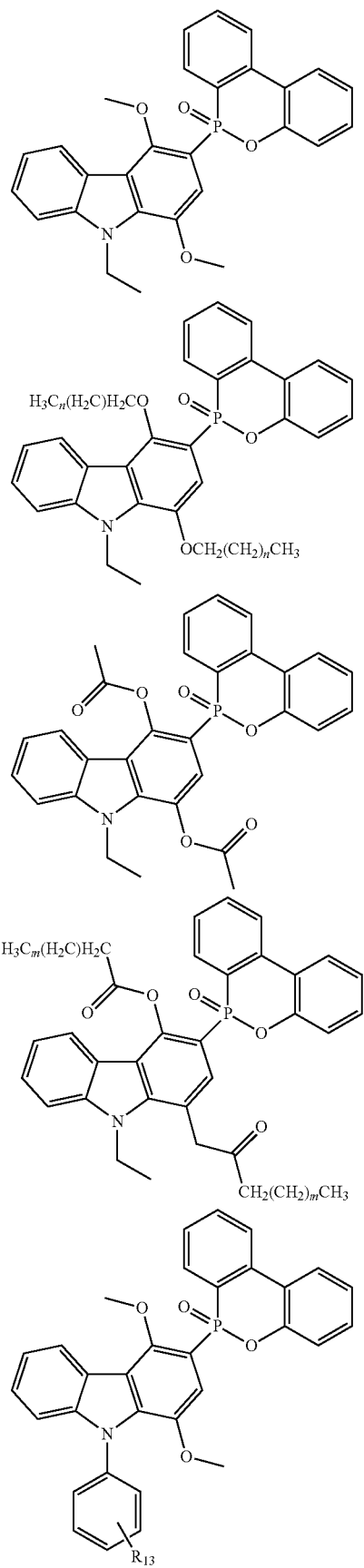
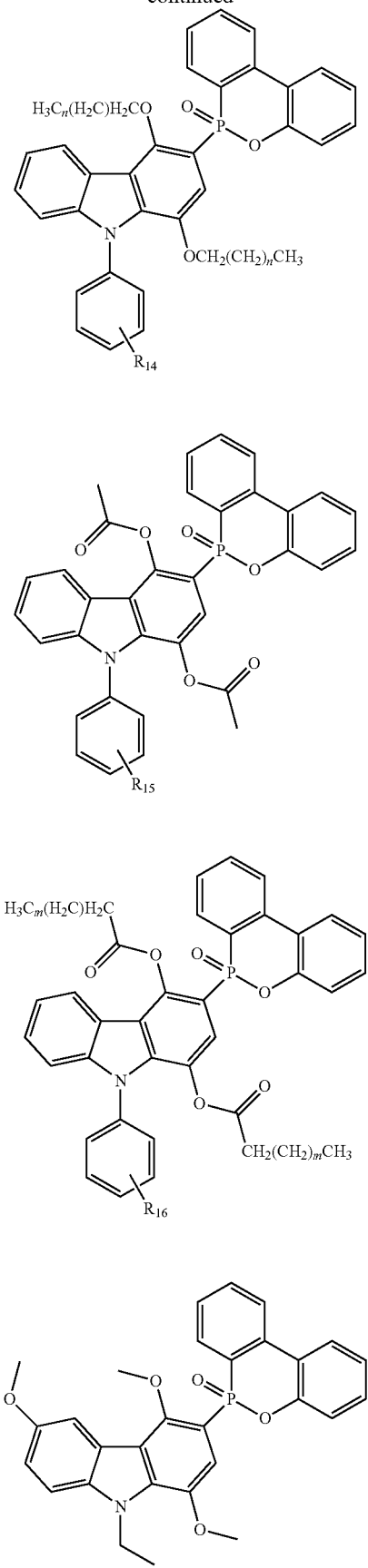

-continued
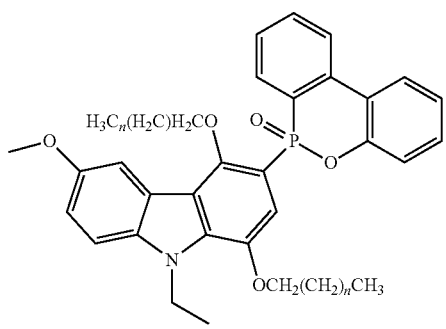
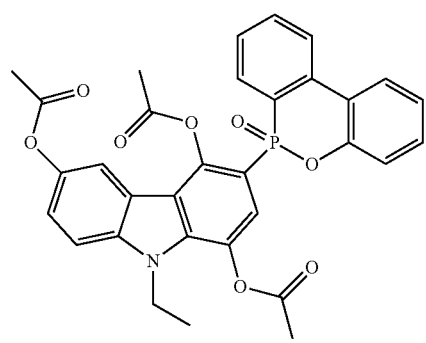
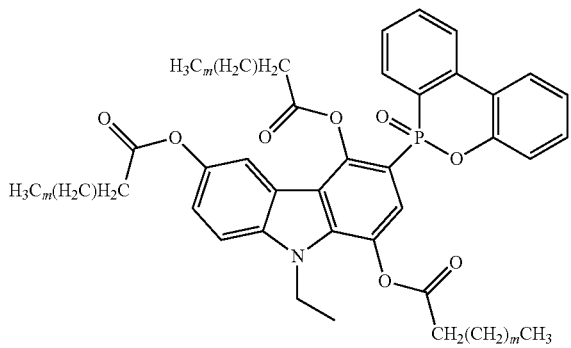
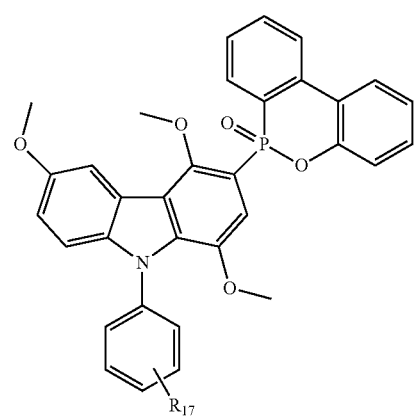
-continued
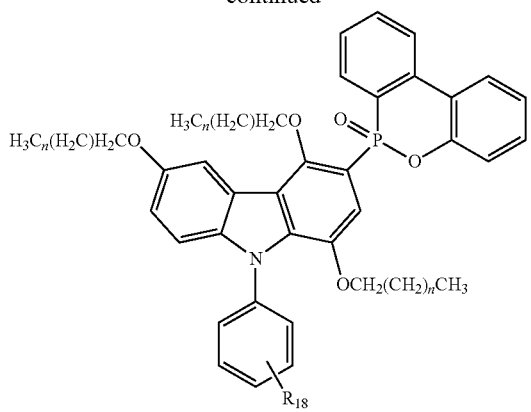
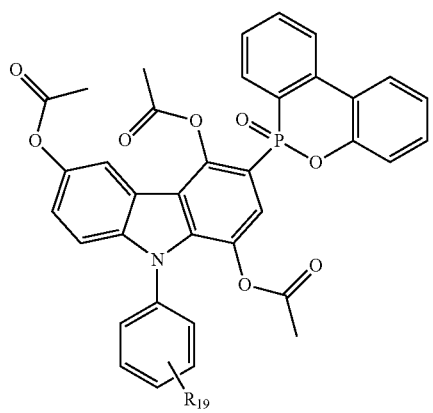
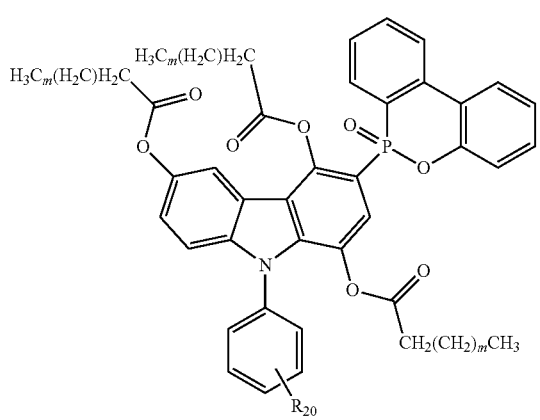
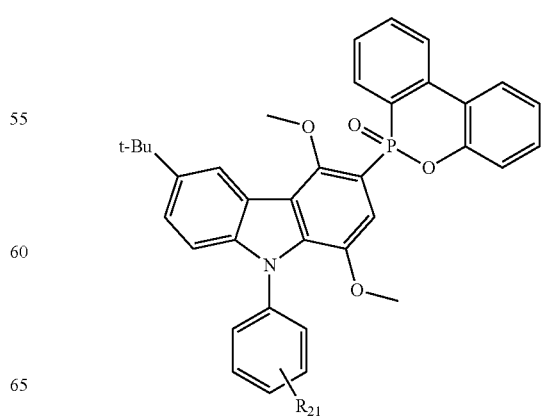

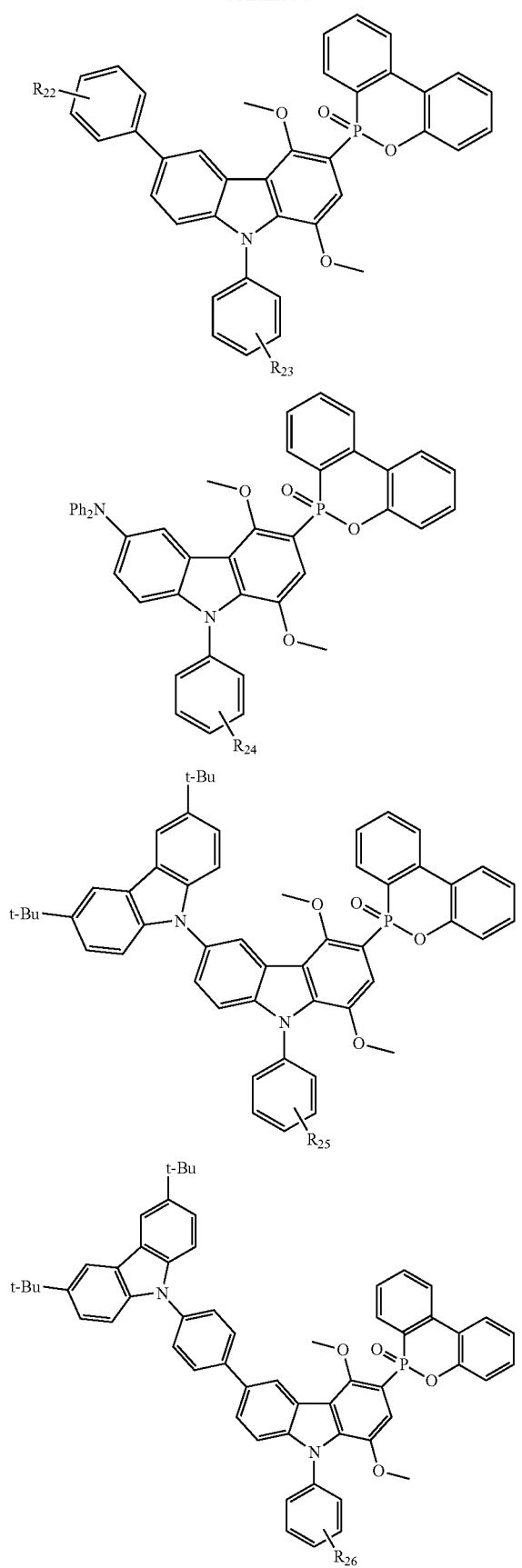
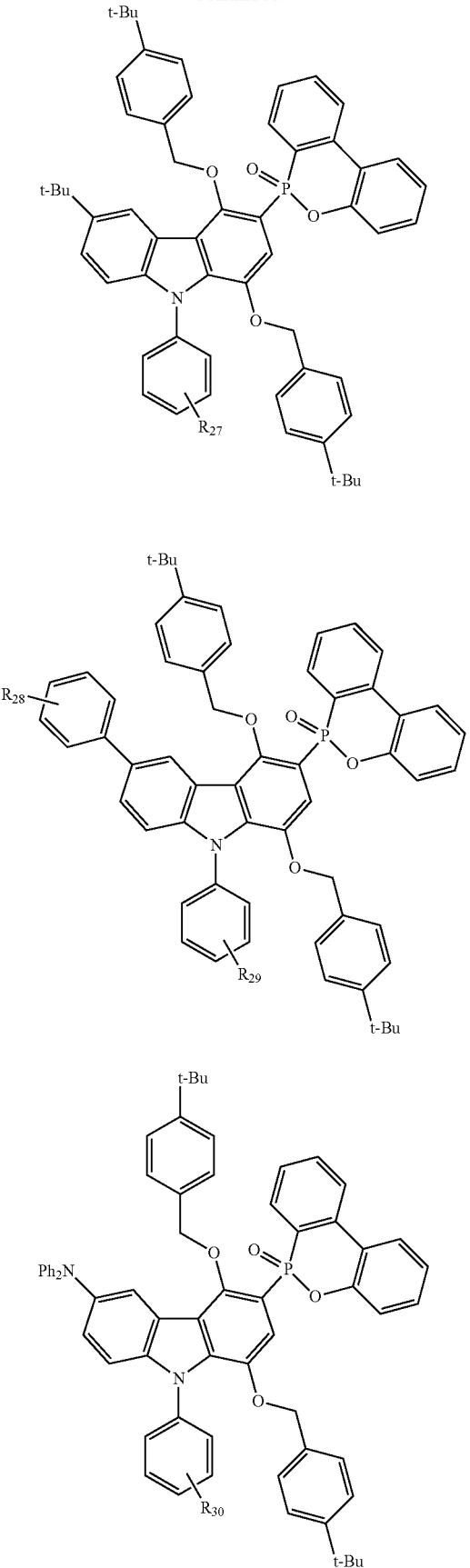

45
-continued
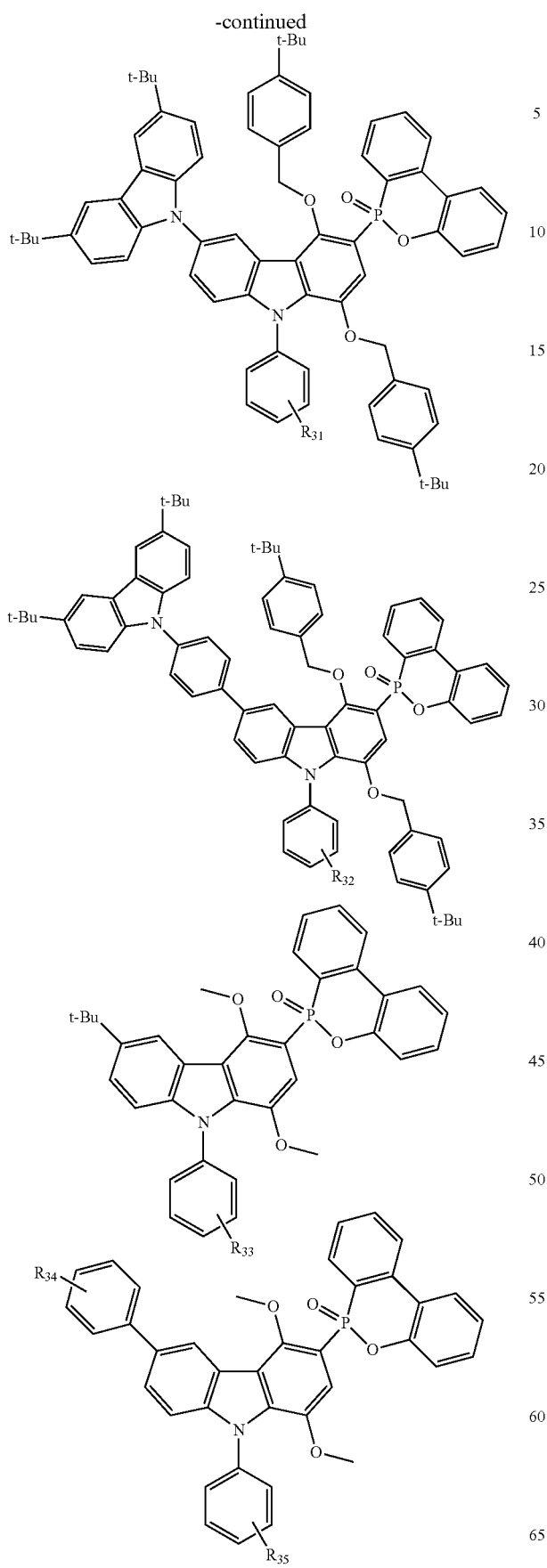
46
-continued
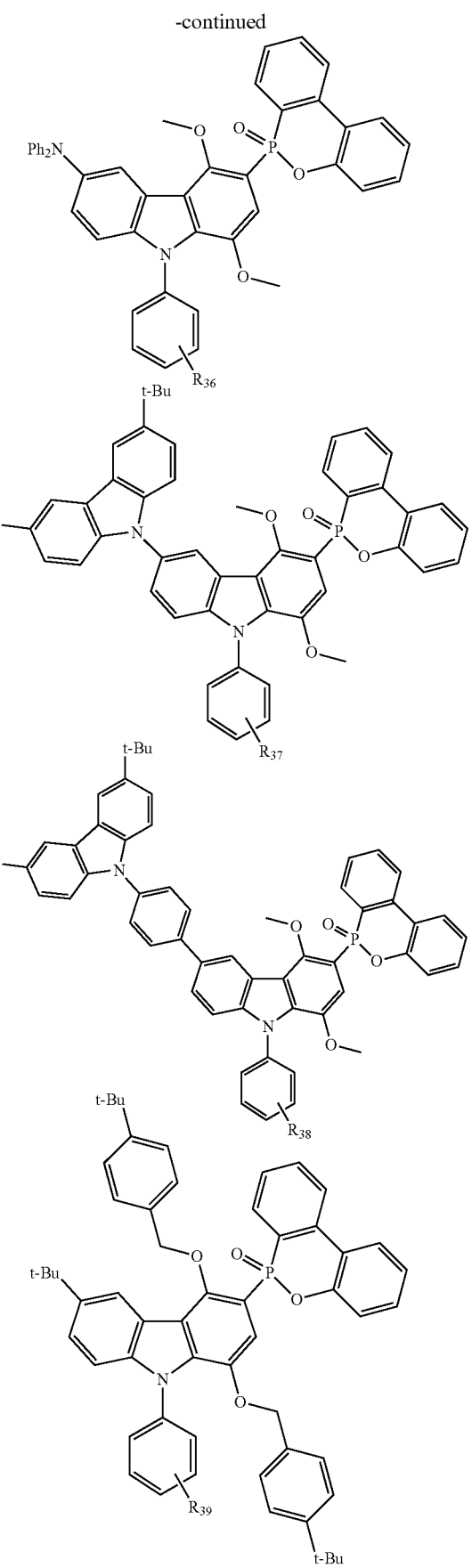

47
-continued
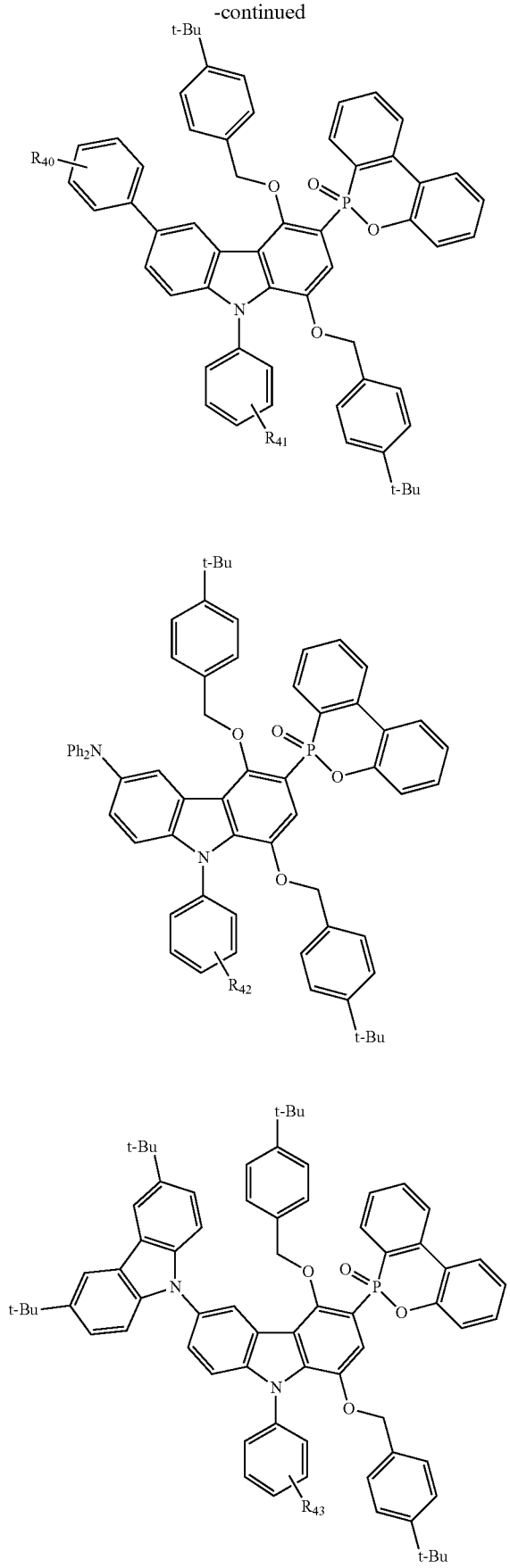
48
-continued
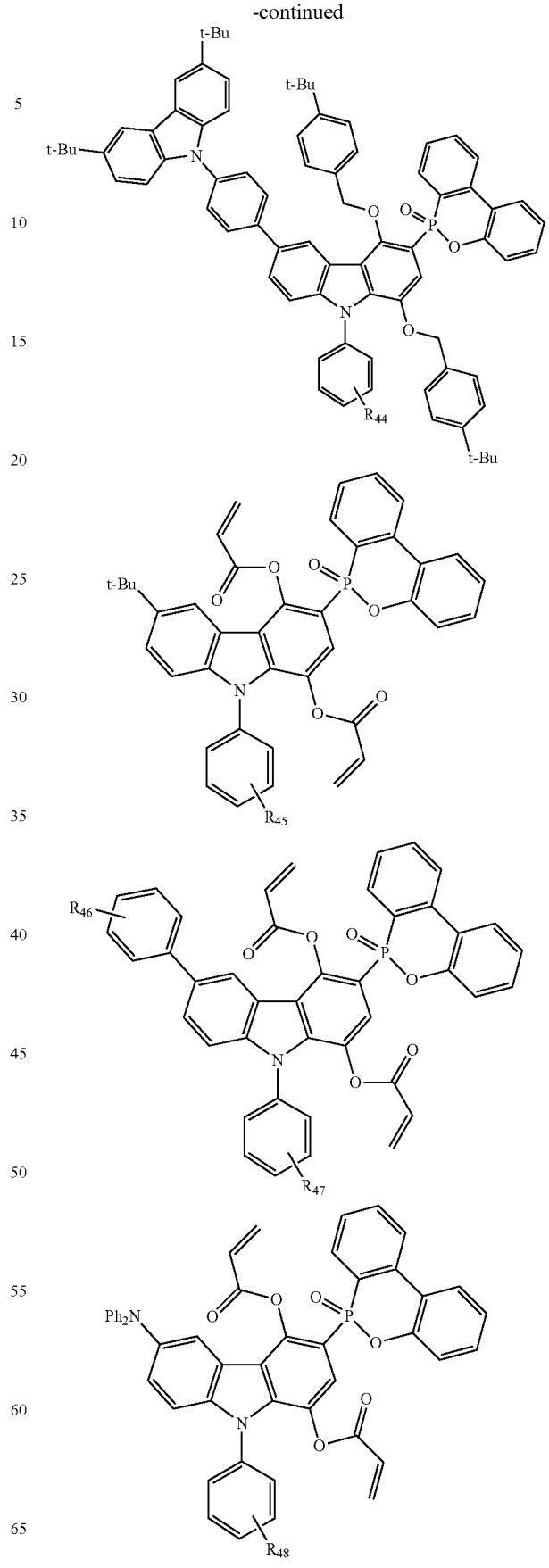

49
-continued
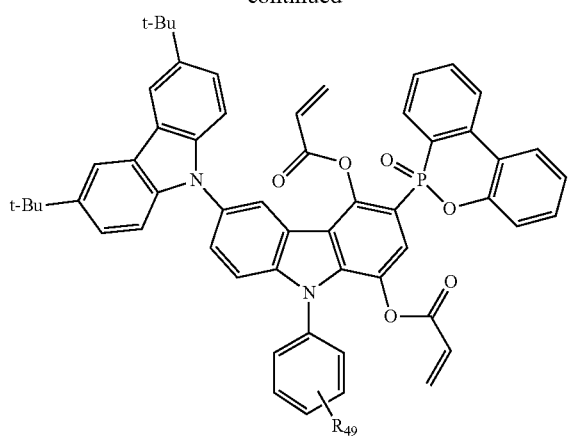
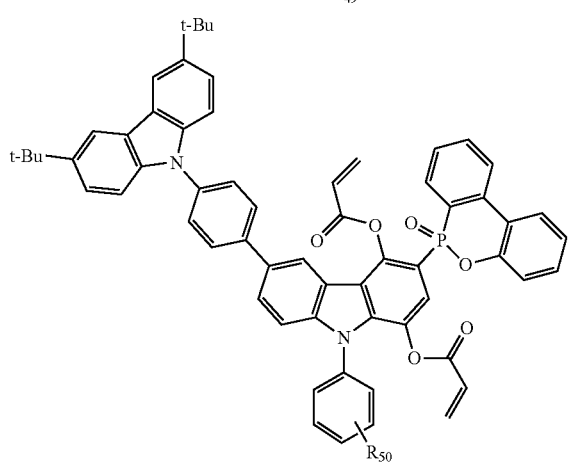
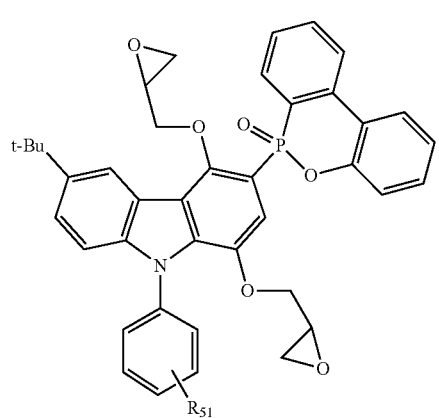
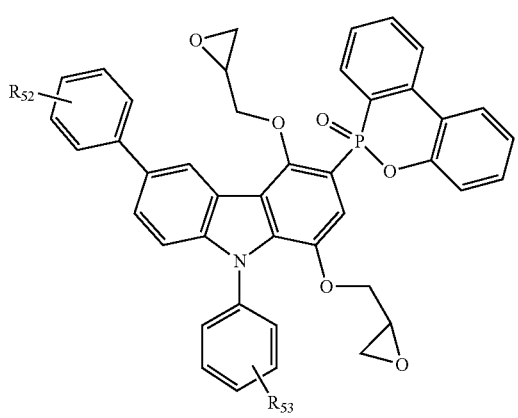
50
-continued
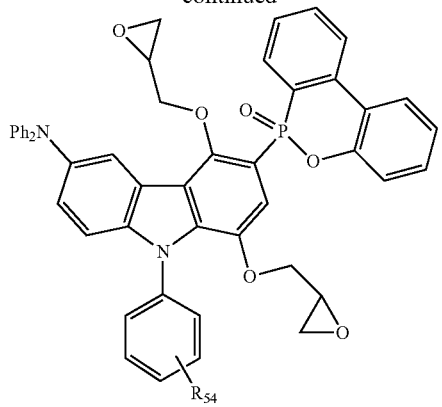
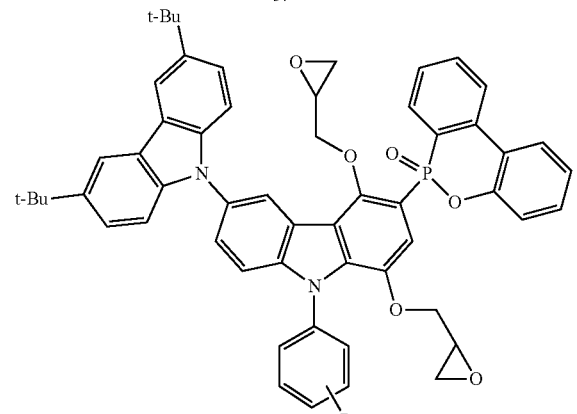
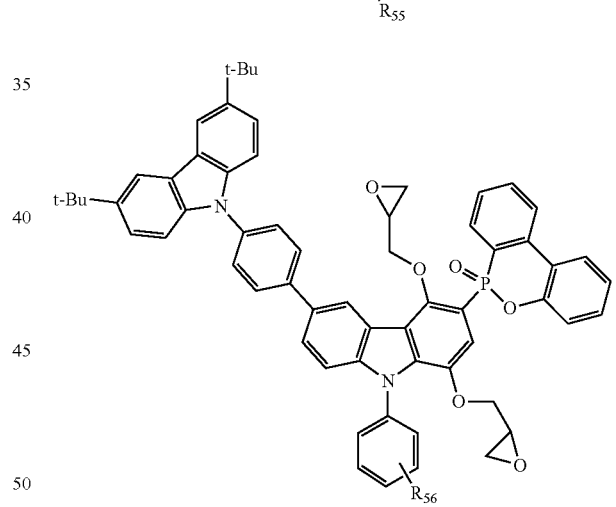
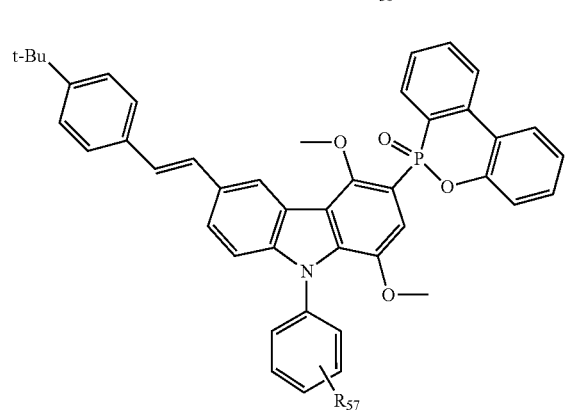

51
-continued
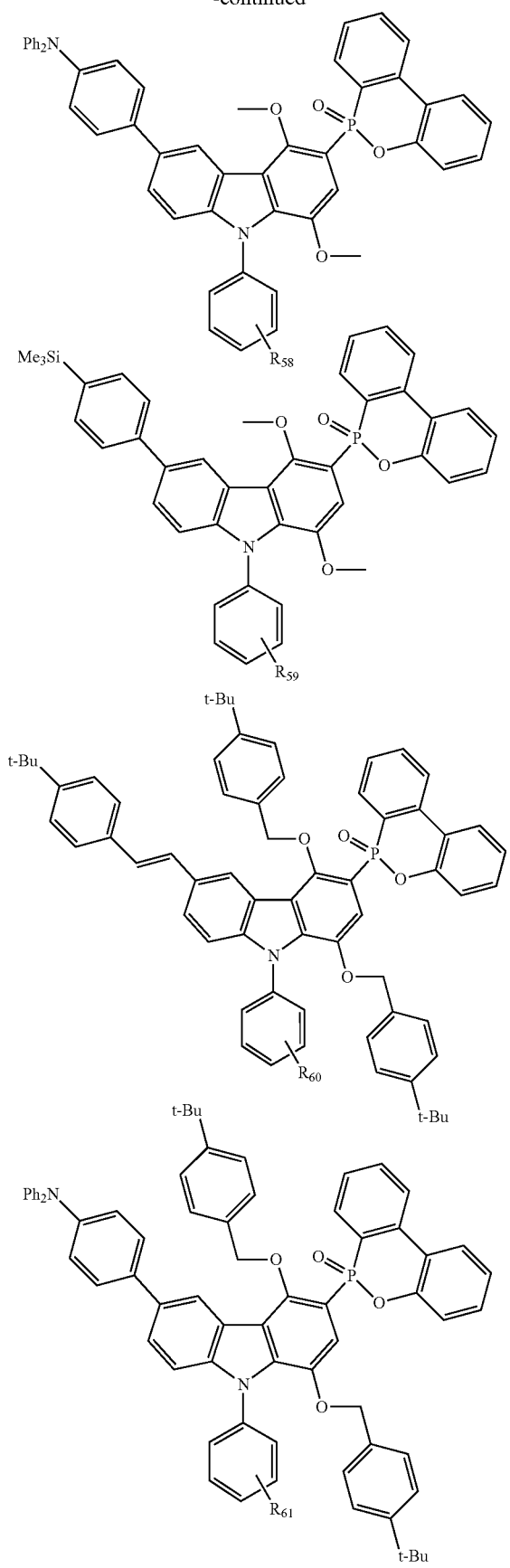
52
-continued
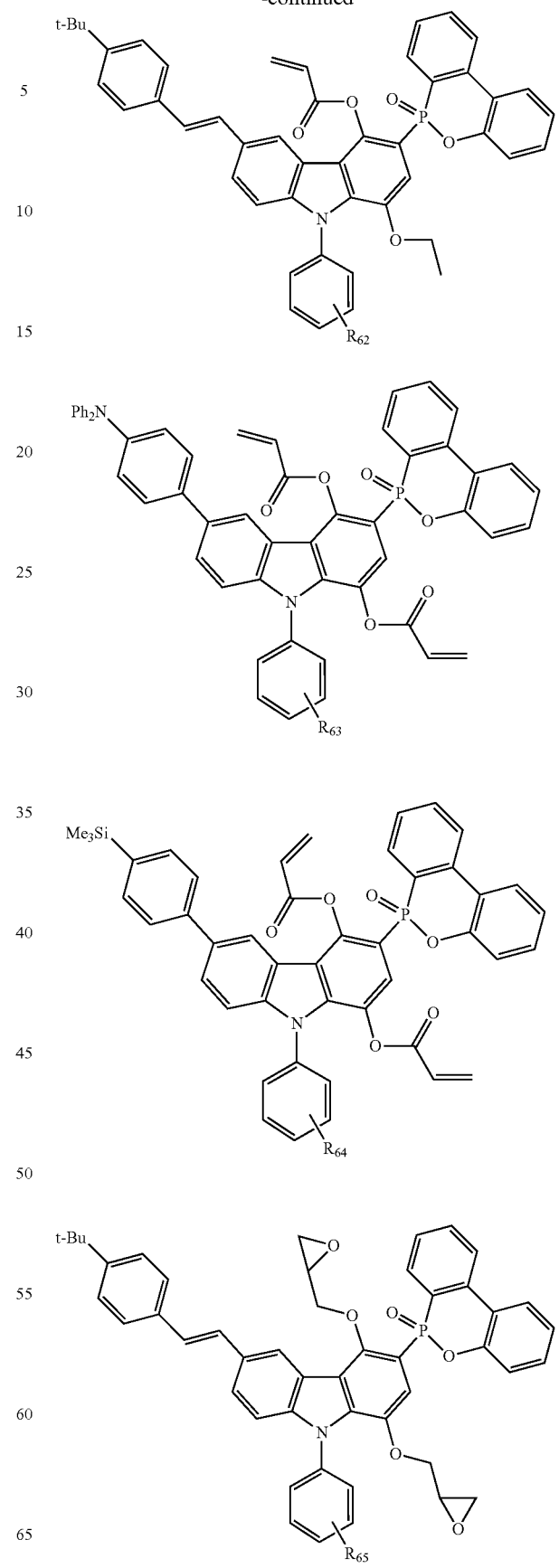

53
-continued
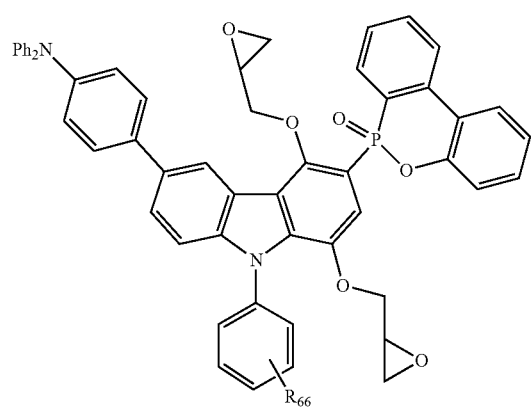
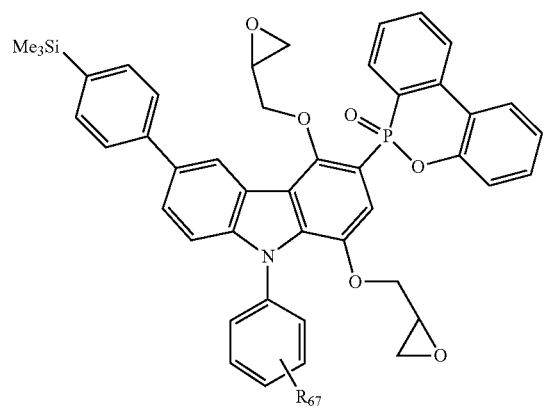
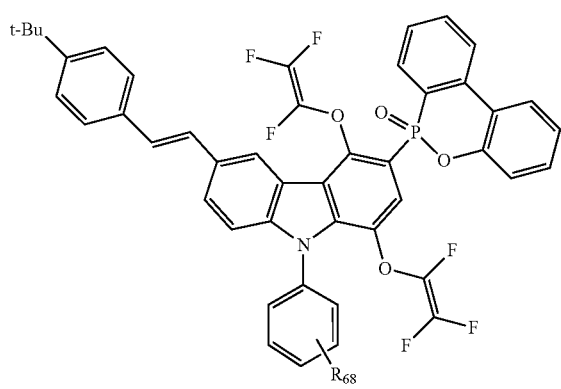
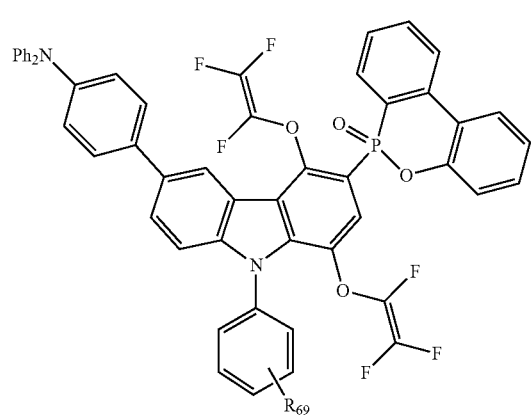
54
-continued
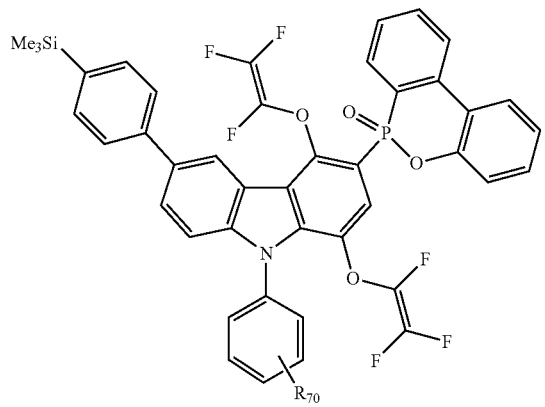
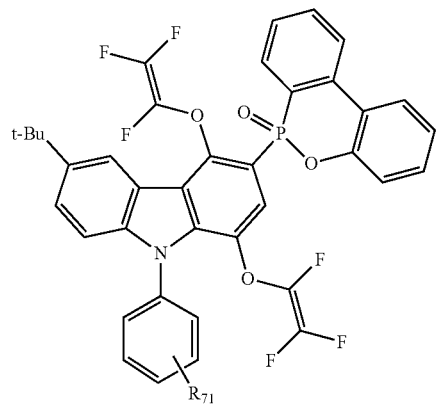
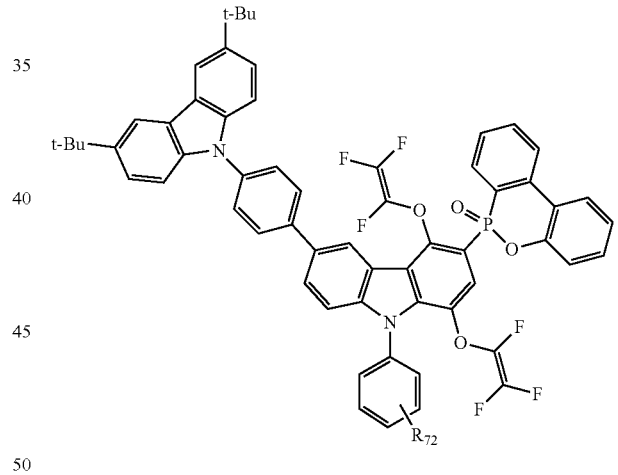
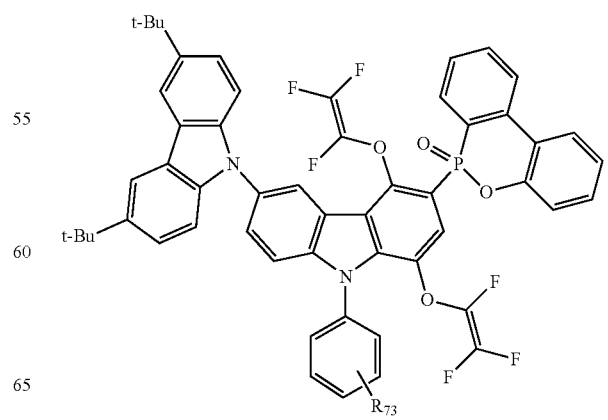

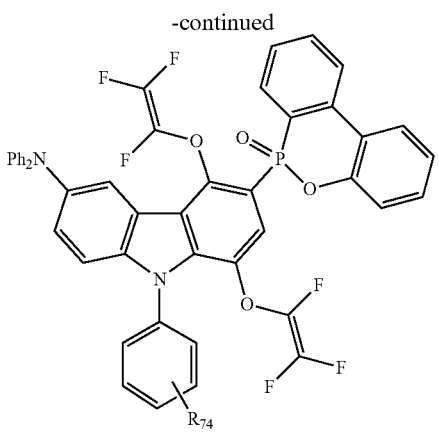

n and m each are independently an integer of 0 to 10, $R_{13}$ to $R_{74}$ each are independently hydrogen, $(C_5-C_{30})$ aryl, $(C_3-C_{30})$heteroaryl, $(C_2-C_{10})$alkenyl, $(C_2-C_{18})$alkynyl, straight- or branched-chain $(C_1-C_{22})$alkyl, straight- or branched-chain saturated or unsaturated $(C_1-C_{22})$alkyl including oxygen, nitrogen, or sulfur, $(C_1-C_{22})$alkoxy, $(C_3-C_{22})$cycloalkyl, $(C_3-C_{22})$cycloalkyl$(C_1-C_{22})$alkyl, halogen, cyano, amino, mono- or di-$(C_1-C_{10})$alkylamino, mono- or di-$(C_6-C_{12})$arylamino, hydroxyl, mono- or di-benzylamino, or mono- or di-$(C_3-C_{10})$cycloalkylamino.

3. A light-emitting device comprising the phosphaphenanthrene-carbazole-based organic light-emitting compound of claim 1.

4. The light-emitting device of claim 3, wherein the phosphaphenanthrene-carbazole-based organic light-emitting compound is included in at least one layer selected from a group consisting of a hole injection layer, a hole transfer layer, an electron injection layer, an electron transfer layer, a light emitting layer, and a mixed function layer thereof.

5. A light-emitting device comprising a first electrode, a second electrode, and at least one organic layer disposed between the first and second electrodes, wherein at least one of the organic layers includes the phosphaphenanthrene-carbazole-based organic light-emitting compound of claim 1.

6. The light-emitting device of claim 5, wherein the organic layer includes at least one layer selected from a group consisting of a hole injection layer, a hole transfer layer, an electron injection layer, an electron transfer layer, and a mixed function layer thereof and a light emitting layer.

7. The light-emitting device of claim 6, wherein the phosphaphenanthrene-carbazole-based organic light-emitting compound is included in at least one of the electron transport layer and the light emitting layer.

8. A light-emitting device comprising the phosphaphenanthrene-carbazole-based organic light-emitting compound of claim 2.

9. The light-emitting device of claim 8, wherein the phosphaphenanthrene-carbazole-based organic light-emitting compound is included in at least one layer selected from a group consisting of a hole injection layer, a hole transfer layer, an electron injection layer, an electron transfer layer, a light emitting layer, and a mixed function layer thereof.

10. A light-emitting device comprising a first electrode, a second electrode, and at least one organic layer disposed between the first and second electrodes,
wherein at least one of the organic layers includes the phosphaphenanthrene-carbazole-based organic light-emitting compound of claim 8.

11. The light-emitting device of claim 10, wherein the organic layer includes at least one layer selected from a group consisting of a hole injection layer, a hole transfer layer, an electron injection layer, an electron transfer layer, and a mixed function layer thereof and a light emitting layer.

12. The light-emitting device of claim 11, wherein the phosphaphenanthrene-carbazole-based organic light-emitting compound is included in at least one of the electron transport layer and the light emitting layer.

* * * * *